United States Patent
Nakazato

(10) Patent No.: US 10,016,123 B2
(45) Date of Patent: Jul. 10, 2018

(54) METHOD OF INSERTING TREATMENT TOOL

(71) Applicant: OLYMPUS CORPORATION, Tokyo (JP)

(72) Inventor: Takeharu Nakazato, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 96 days.

(21) Appl. No.: 14/798,978

(22) Filed: Jul. 14, 2015

(65) Prior Publication Data

US 2017/0014116 A1    Jan. 19, 2017

(51) Int. Cl.
*A61B 1/00* (2006.01)
*A61B 1/273* (2006.01)
(Continued)

(52) U.S. Cl.
CPC .......... *A61B 1/273* (2013.01); *A61B 1/00098* (2013.01); *A61B 1/018* (2013.01); *A61B 1/2736* (2013.01); *A61B 8/0841* (2013.01); *A61B 8/12* (2013.01); *A61F 2/95* (2013.01); *A61B 2017/00278* (2013.01); *A61B 2017/00818* (2013.01); *A61M 2025/018* (2013.01); *A61M 2025/0183* (2013.01)

(58) Field of Classification Search
CPC . A61B 1/00071; A61B 1/00087; A61B 1/005; A61B 1/012; A61B 1/018; A61B 1/273; A61B 1/2736; A61B 1/00098; A61B 1/00089; A61B 2017/00818; A61B 2017/00278; A61B 1/00177

USPC ........................................................ 600/107
See application file for complete search history.

(56) References Cited

U.S. PATENT DOCUMENTS 9,757,103 B2 * 9/2017 Yokota ............. A61B 17/00234
2003/0040657 A1 * 2/2003 Yamaya ............. A61B 1/00039
                                                        600/107
(Continued)

FOREIGN PATENT DOCUMENTS

JP      2000-350785 A    12/2000
JP      2006-212453 A     8/2006
(Continued)

*Primary Examiner* — Ryan Henderson
*Assistant Examiner* — Pamela F Wu
(74) *Attorney, Agent, or Firm* — Scully, Scott, Murphy & Presser, P.C.

(57) ABSTRACT

A method of inserting a treatment tool includes: making a puncture needle project from a first channel of an endoscope and puncturing an upper digestive tract to place a distal end of a needle tube of the puncture needle inside a biliary tract while observing an ultrasound image; inserting a guide wire into the biliary tract via the needle tube and making a distal end of the guide wire extend out from a duodenal papilla into a duodenum; placing a distal end portion of the endoscope in vicinity of the duodenal papilla while keeping the distal end of the guide wire extending out from the duodenal papilla while observing a captured image; pulling the guide wire extending out from the duodenal papilla into a second channel having a raised angle of the treatment tool larger than that of the first channel; and inserting the treatment tool inside the biliary tract via the guide wire.

12 Claims, 21 Drawing Sheets

(51) Int. Cl.
   *A61B 1/018*   (2006.01)
   *A61B 8/12*    (2006.01)
   *A61F 2/95*    (2013.01)
   *A61B 8/08*    (2006.01)
   A61B 1/04      (2006.01)
   A61B 17/00     (2006.01)
   A61M 25/01     (2006.01)

(56) References Cited

U.S. PATENT DOCUMENTS

| | | | |
|---|---|---|---|
| 2008/0051626 A1 | 2/2008 | Sato et al. | |
| 2010/0099947 A1 | 4/2010 | Sato et al. | |
| 2011/0313242 A1* | 12/2011 | Surti | A61B 1/00089 600/104 |
| 2015/0011834 A1* | 1/2015 | Ayala | A61B 17/0218 600/208 |
| 2015/0012008 A1* | 1/2015 | McWeeney | A61M 25/0136 606/108 |
| 2016/0135941 A1* | 5/2016 | Binmoeller | A61F 2/04 623/23.7 |

FOREIGN PATENT DOCUMENTS

| | | |
|---|---|---|
| JP | 2008-043616 A | 2/2008 |
| JP | 2012-210429 A | 11/2012 |

* cited by examiner

METHOD OF INSERTING TREATMENT TOOL

BACKGROUND OF THE INVENTION

1. Field of the Invention

The present invention relates to a method for inserting the treatment tool into a biliary tract from a digestive tract.

2. Description of the Related Art

In the related art, various kinds of endoscopes are used at the time of observing internal organs of a subject such as a patient. Among these endoscopes, there is a known ultrasound endoscope that transmits ultrasound waves to an observation target and receives echoes of the ultrasound waves reflected at the observation target. An ultrasound image of the observation target is generated by applying predetermined signal processing to the ultrasound echoes received by the ultrasound endoscope, thereby achieving to perform diagnosis and treatment while observing the ultrasound image.

As a treatment method using the ultrasound endoscope, there is a method of inserting a treatment tool in which the treatment tool is inserted into a stenosis at a biliary tract from a digestive tract. According to this method of inserting a treatment tool, for example, a stent is inserted into a stenosis portion $Cb_{st}$ of the biliary tract (common bile duct Cb) by using, for example, an ultrasound endoscope (EUS scope) and a scope for a duodenum (JF scope). FIGS. 1 to 6 are explanatory diagrams for a method of inserting a treatment tool in the related art, and are the diagrams for explaining the method of inserting a treatment tool in which the treatment tool is inserted into the biliary tract from the digestive tract. First, as illustrated in FIG. 1, an EUS scope 200 is inserted into a duodenum Dd inside a subject, and an image is captured from the duodenum Dd to a common bile duct Cb by ultrasound waves, and then a bile duct is punctured with a cylindrical-shaped puncture needle TD100. The technology of performing puncture while observing an ultrasound image by the EUS scope is referred to as an endoscopic ultrasound-guided fine needle aspiration (FNA).

After that, a contrast agent is injected into the common bile duct Cb via the puncture needle TD100, and a guide wire GW100 is inserted into the common bile duct Cb via the puncture needle TD100 while performing radiographic visualization. Then, a distal end of the guide wire GW100 is placed inside the duodenum Dd via a duodenal papilla Dp (refer to FIG. 2).

After placement of the distal end of guide wire GW100 inside the duodenum Dd, the puncture needle TD100 and the EUS scope 200 are taken out from the inside of the subject while leaving the guide wire GW100 inside the subject (refer to FIG. 3). In a state that only the guide wire GW100 is left inside the subject, a JF scope 201 is inserted into the duodenum Dd (refer to FIG. 4) and the guide wire GW100 extending from the duodenal papilla Dp is pulled into the JF scope 201 (refer to FIG. 5). This results in a state that the guide wire GW100 extends from the JF scope 201 and the other end of the guide wire GW100 is placed inside the common bile duct Cb. A cylindrical-shaped stent ST100 is placed at the duodenal papilla Dp and the stenosis portion $Cb_{st}$ via the JF scope 201 and the guide wire GW100 in this state, thereby achieving a state that the stenosis portion $Cb_{st}$ is expanded by the stent ST100 (refer to FIG. 6). Treatment can be performed inside the biliary tract including the common bile duct Cb through the stent ST100.

Examples of the most general method of inserting a treatment tool into the stenosis at the biliary tract include a technique of "endoscopic retrograde cholangiopancreatography (ERCP)" in which a cannula is inserted into the duodenal papilla Dp while visualizing an endoscopic optical image by using the JF scope, and a contrast agent is injected into the bile duct, etc. via the cannula so as to make a state that the biliary tract, etc. can be observed by radiographic visualization. According to this technology, for example, the guide wire GW100 is placed in the common bile duct Cb via the cannula while the cannula is inserted into the duodenal papilla Dp, and the cylindrical-shaped stent ST100 is placed in the duodenal papilla Dp and the stenosis portion $Cb_{st}$ via the JF scope 201 and the guide wire GW100. However, the method of inserting a treatment tool by utilizing this ERCP is known as a highly difficult method among the endoscopic procedures, and there may be a case where the guide wire GW100 cannot be inserted into the common bile duct Cb. As a replaceable procedure, there is a method of inserting a treatment tool by using the above-described EUS scope.

SUMMARY OF THE INVENTION

A method of inserting a treatment tool according to one aspect of the invention includes: making a puncture needle project from a first channel of an endoscope and puncturing an upper digestive tract to place a distal end of a needle tube of the puncture needle inside a biliary tract while observing an ultrasound image; inserting a guide wire into the biliary tract via the needle tube and making a distal end of the guide wire extend out from a duodenal papilla into a duodenum; placing a distal end portion of the endoscope in vicinity of the duodenal papilla while keeping the distal end of the guide wire extending out from the duodenal papilla while observing a captured image; pulling the guide wire extending out from the duodenal papilla into a second channel having a raised angle of the treatment tool larger than that of the first channel; and inserting the treatment tool inside the biliary tract via the guide wire.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Modes for carrying out the present invention (hereinafter referred to as "embodiment(s)") will be described below in detail with reference to the drawings. The present invention is not limited by the embodiments below. Each of the drawings referred to in the following description only schematically illustrates a shape, a size, and a positional relationship to an extent to be able to understand the content of the present invention. Therefore, the present invention is not limited only to the shape, size, and positional relationship illustrated in each of the drawings.

Embodiments

Figure 1:
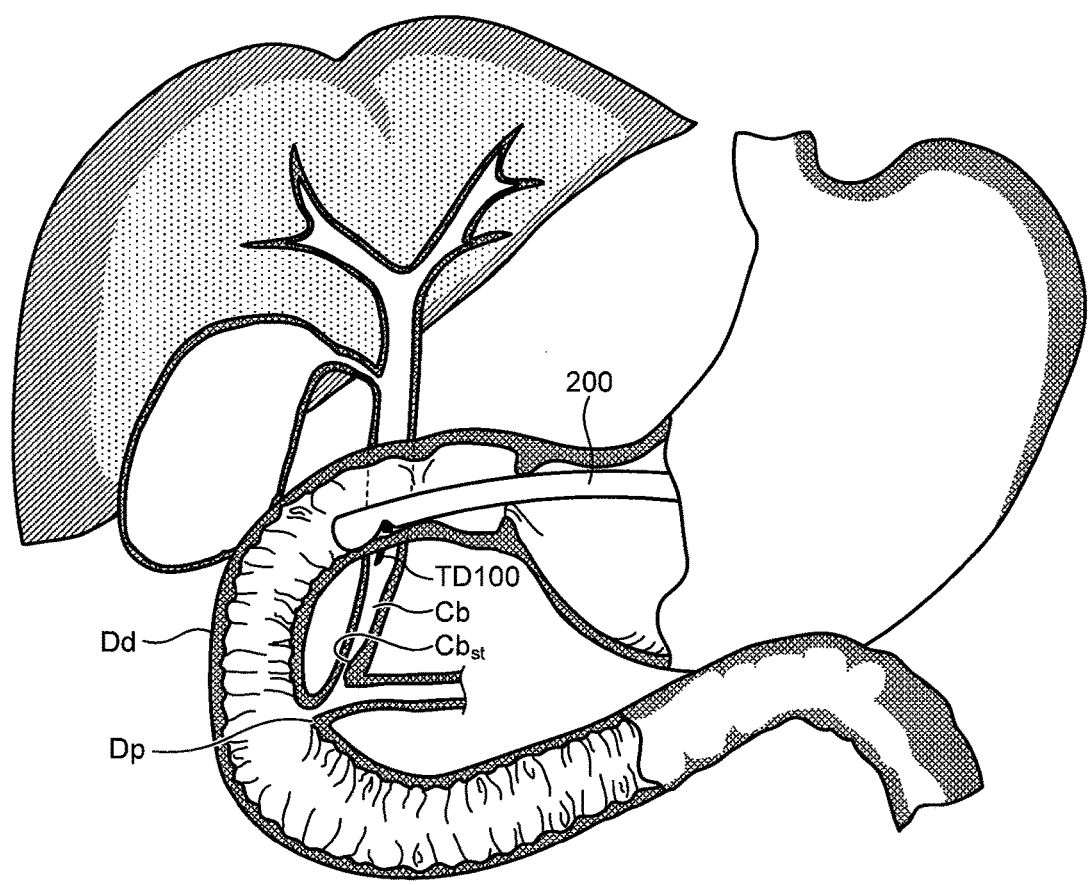
FIG. 1 is an explanatory diagram for a method of inserting a treatment tool in the related art.
Figure 2:
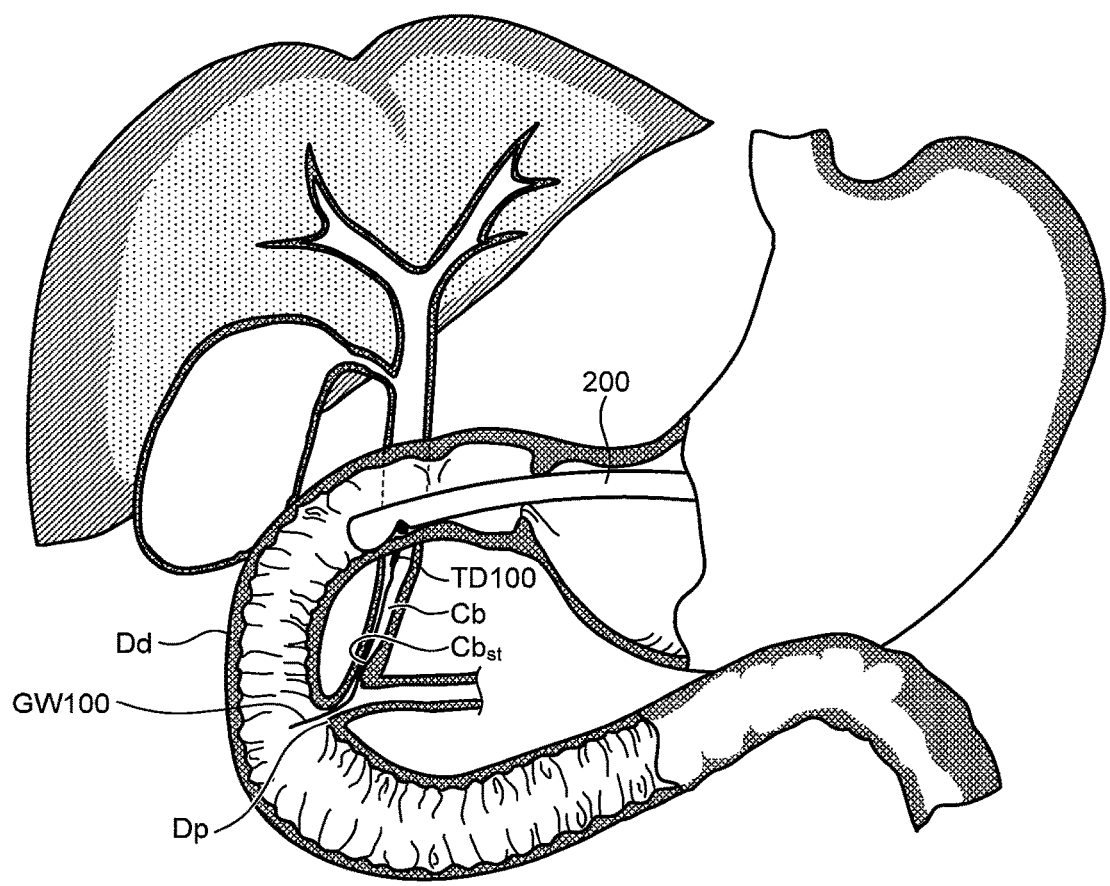
FIG. 2 is an explanatory diagram for the method of inserting a treatment tool in the related art.
Figure 3:
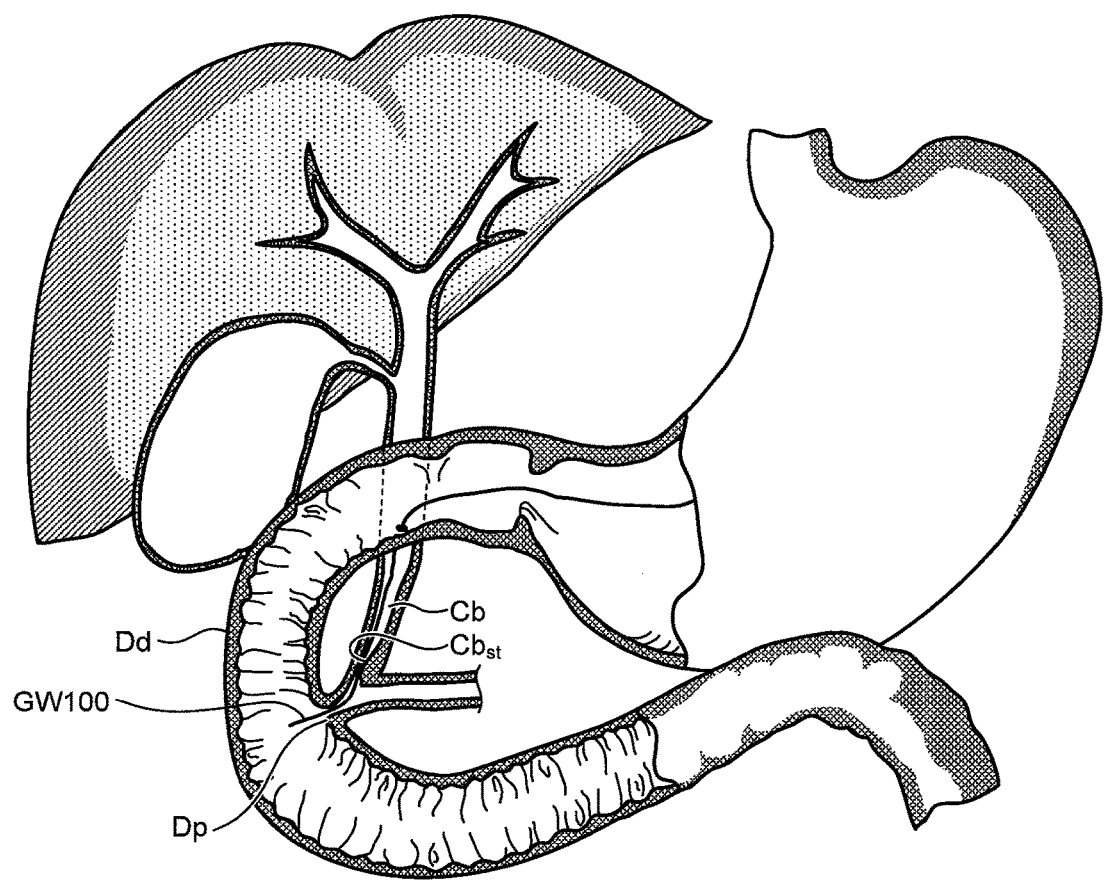
FIG. 3 is an explanatory diagram for the method of inserting a treatment tool in the related art.
Figure 4:
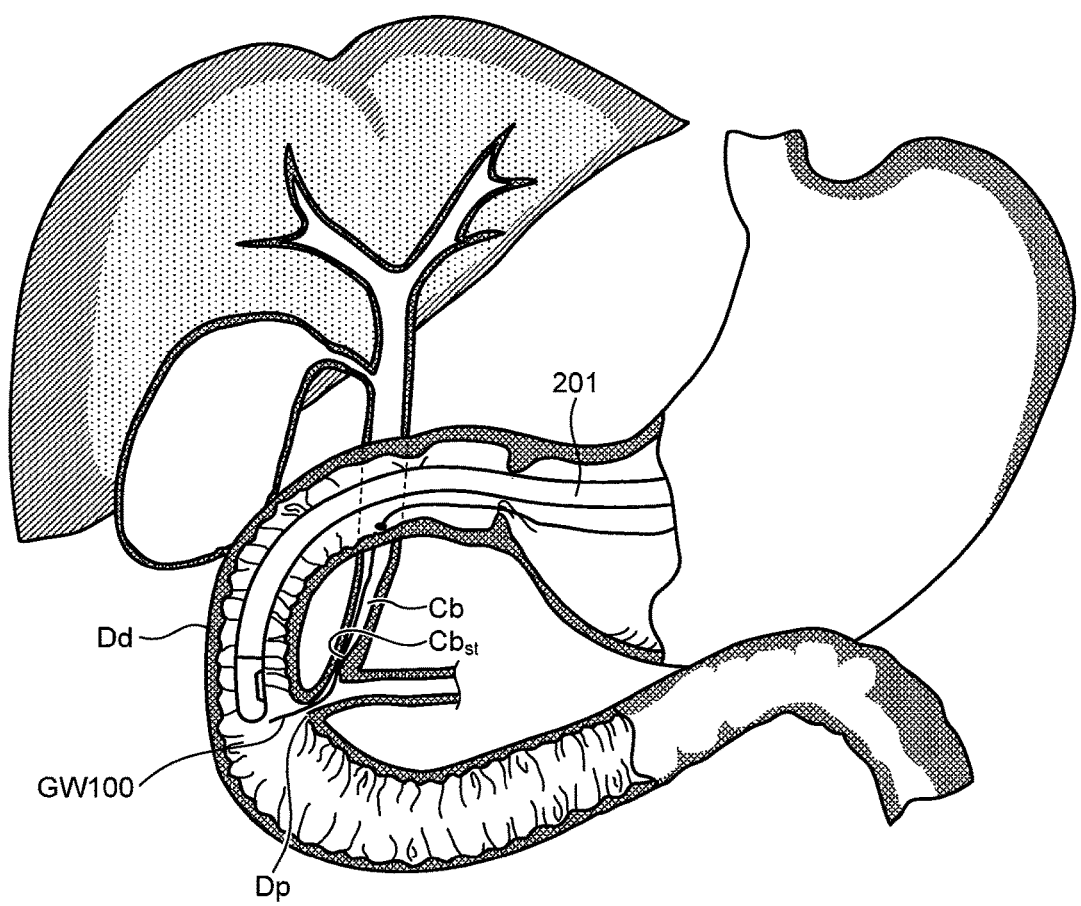
FIG. 4 is an explanatory diagram for the method of inserting a treatment tool in the related art.
Figure 5:
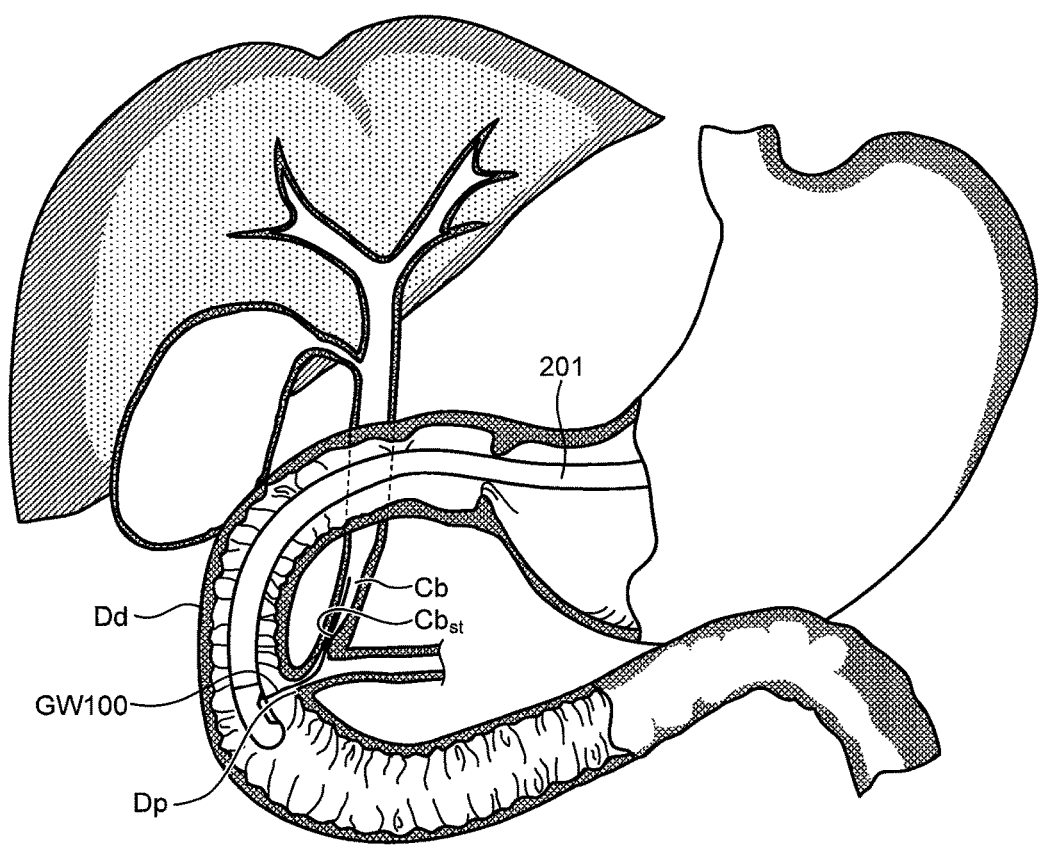
FIG. 5 is an explanatory diagram for the method of inserting a treatment tool in the related art.
Figure 6:
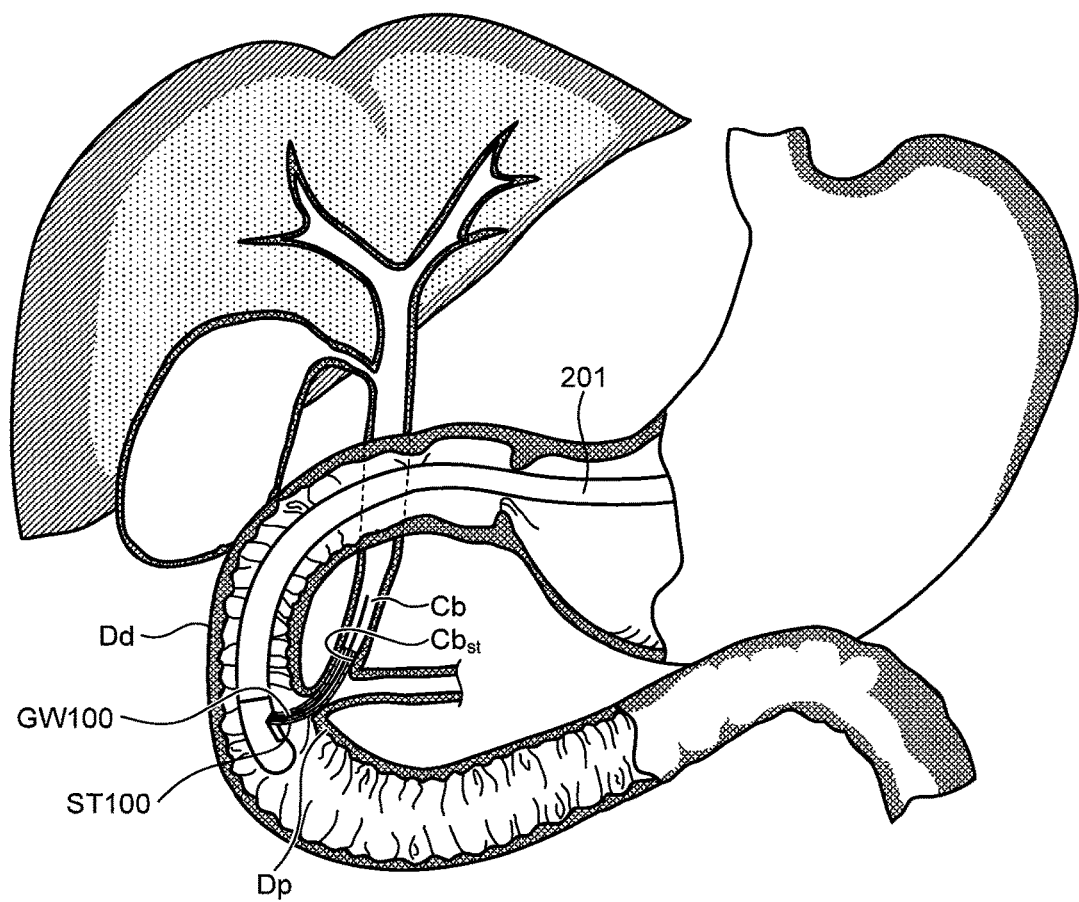
FIG. 6 is an explanatory diagram for the method of inserting a treatment tool in the related art.
Figure 7:
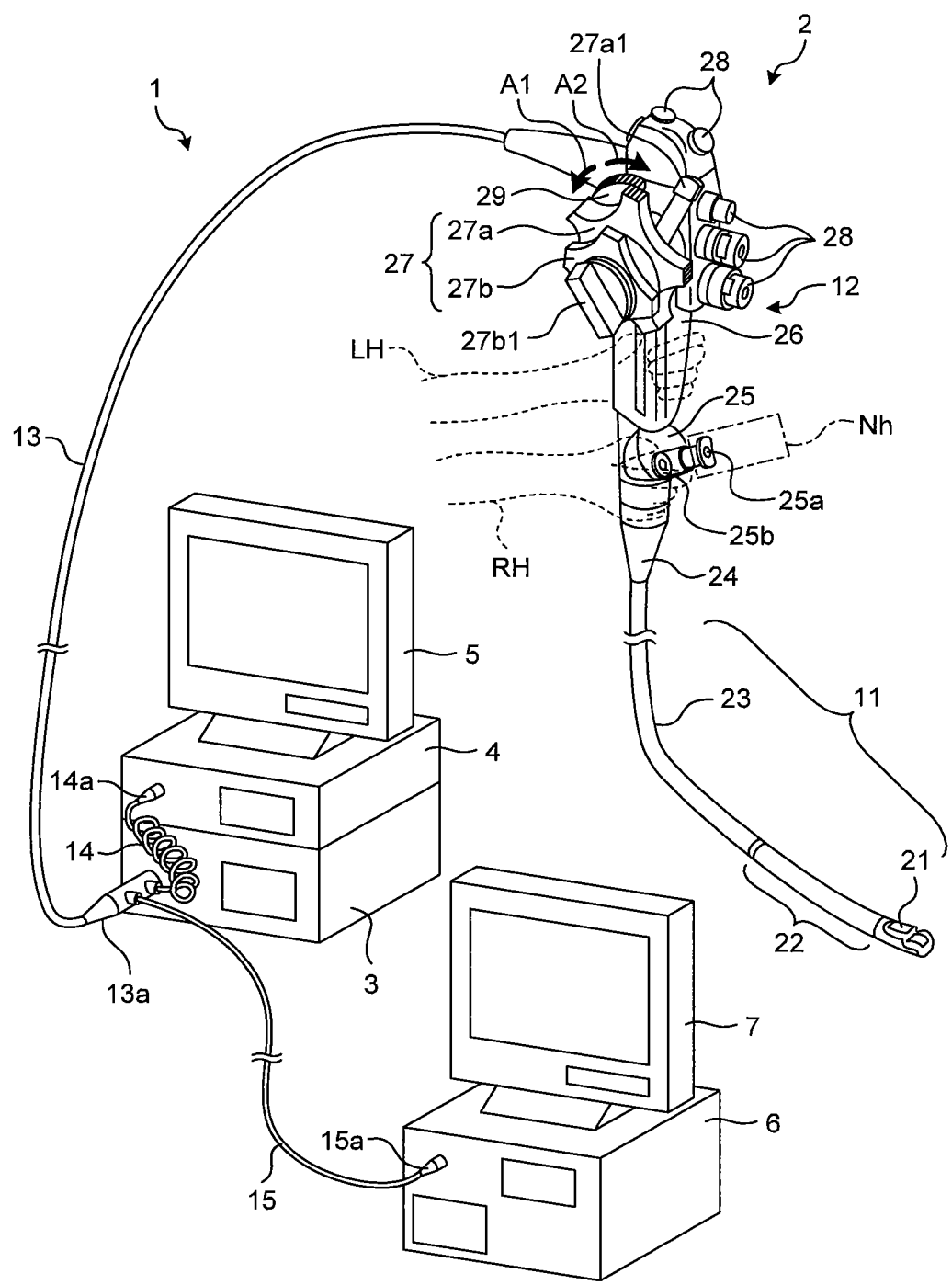
FIG. 7 is a schematic diagram illustrating a structure of an endoscope system according to an embodiment of the present invention.

FIG. 7 is a schematic diagram illustrating a structure of an endoscope system according to an embodiment of the present invention. An ultrasound endoscope system 1 includes an ultrasound endoscope (hereinafter also referred to simply as an endoscope) 2, a light source device 3, a video processor 4, an optical image display monitor 5, an ultrasound observation device 6, and an ultrasound image display monitor 7.

The endoscope 2 includes an inserting portion 11, an operation unit 12 from which the inserting portion 11 extends, and a universal cord 13 extending from the operating unit 12. The inserting portion 11 extends in a longitudinal direction, and is formed so as to be inserted into a living body. The universal cord 13 is connected to the light source device 3 via a scope connector 13a disposed at a proximal end. A coiled scope cable 14 and an ultrasound signal cable 15 extend from this scope connector 13a. Further, an electric connector 14a is provided at one end of the scope cable 14, and the electric connector 14a is connected to the video processor 4. Further, an ultrasound connector 15a is provided at one end of the ultrasound signal cable 15, and the ultrasound connector 15a is connected to the ultrasound observation device 6.

The inserting portion 11 is formed by connecting a distal end portion 21, a curved portion 22, and a flexible portion 23 sequentially from a distal end. On a side surface of the distal end portion 21, two channel opening portions, an optical observation window, an optical light window, an ultrasound transducer unit, etc. described later are disposed.

The operating unit 12 is formed by including an anti-breakage portion 24 from which the inserting portion 11 extends, a channel opening setting portion 25, an operating unit body 26 constituting a grip portion, a curve operating unit 27 having two curve operation knobs 27a and 27b disposed in a manner superimposed on an upper surface side of the operating unit body 26, a plurality of switches 28 to provide instructions to execute various functions of the endoscope, and a raising lever 29 to operate a raising base described later.

The channel opening setting portion 25 is disposed at a side portion on a lower side of the operating unit body 26, and provided with two forceps openings 25a and 25b. The respective forceps openings 25a and 25b provided at the channel opening setting portion 25 of the operating unit 12 are in communication with the two channel opening portions provided at the distal end portion 21 of the inserting portion 11 via two treatment tool channels not illustrated provided inside the inserting portion 11. The forceps opening 25a is a channel opening for endoscopic ultrasound-guided fine needle aspiration (FNA), and the forceps opening 25b is a channel opening for endoscopic retrograde cholangiopancreatography (ERCP). A puncture needle handle portion Nh illustrated by a dot-dash-line is attached to the forceps opening 25a.

The two forceps openings 25a and 25b are disposed at the channel opening setting portion 25 such that the forceps opening on a side closer to the right hand RH is the forceps opening 25b and the forceps opening on a side farther from the right hand RH is the forceps opening 25a when an operator puts the right hand RH close to the channel opening setting portion 25.

More specifically, as indicated by dotted lines in FIG. 7, the operator operates the treatment tool inserted into each of the forceps openings with the right hand RH while holding the operating unit body 26 with the left hand LH. The procedure of the ERCP in which a treatment tool such as the cannula for ERCP is inserted into a papilla, is known as a highly difficult method among endoscopic procedures.

Accordingly, the forceps opening 25b for the treatment tool such as the cannula, for which delicate operation is required when the operator holds the operating unit body 26 with the left hand LH, is disposed at the channel opening setting portion 25 so as to be placed more on the operator's right side than the forceps opening 25a.

The curve operation knob 27a is a curving knob for a vertical direction, and the curve operation knob 27b is a curving knob for a horizontal direction. On a proximal end side of the curve operation knob 27a, a curve fixing lever 27a1 is provided to fix a curving state in the vertical direction, and on a distal end side of the curve operation knob 27b, a curve fixing lever 27b1 is provided to fix a curving state in the horizontal direction.

The plurality of switches 28 includes an air and water feed button, a suction button, a freeze button, and so on.

An imaging unit and an illumination unit for obtaining an optical image inside the subject, and the ultrasound transducer unit for obtaining an ultrasound tomographic image inside the subject are provided at the distal end portion 21 of the endoscope 2. Therefore, the operator inserts the endoscope 2 into the subject, and the optical image inside the subject at a desired position inside the subject (hereinafter referred to as a captured image) and the ultrasound tomographic image (hereinafter referred to as an ultrasound image) can be displayed on the monitors 5 and 7 respectively. The imaging unit can be implemented by a charge coupled device (CCD) image sensor or a complementary metal oxide semiconductor (CMOS) image sensor, and may be provided at the distal end of the inserting portion 11 or may be provided at the operating unit 12 to receive observation light via an optical fiber extending from the distal end of the inserting portion 11.

The endoscope 2 according to the embodiment is an endoscope capable of alone performing both the endoscopic ultrasound-guided fine needle aspiration (FNA) and the endoscopic retrograde cholangiopancreatography (ERCP).

Figure 8:
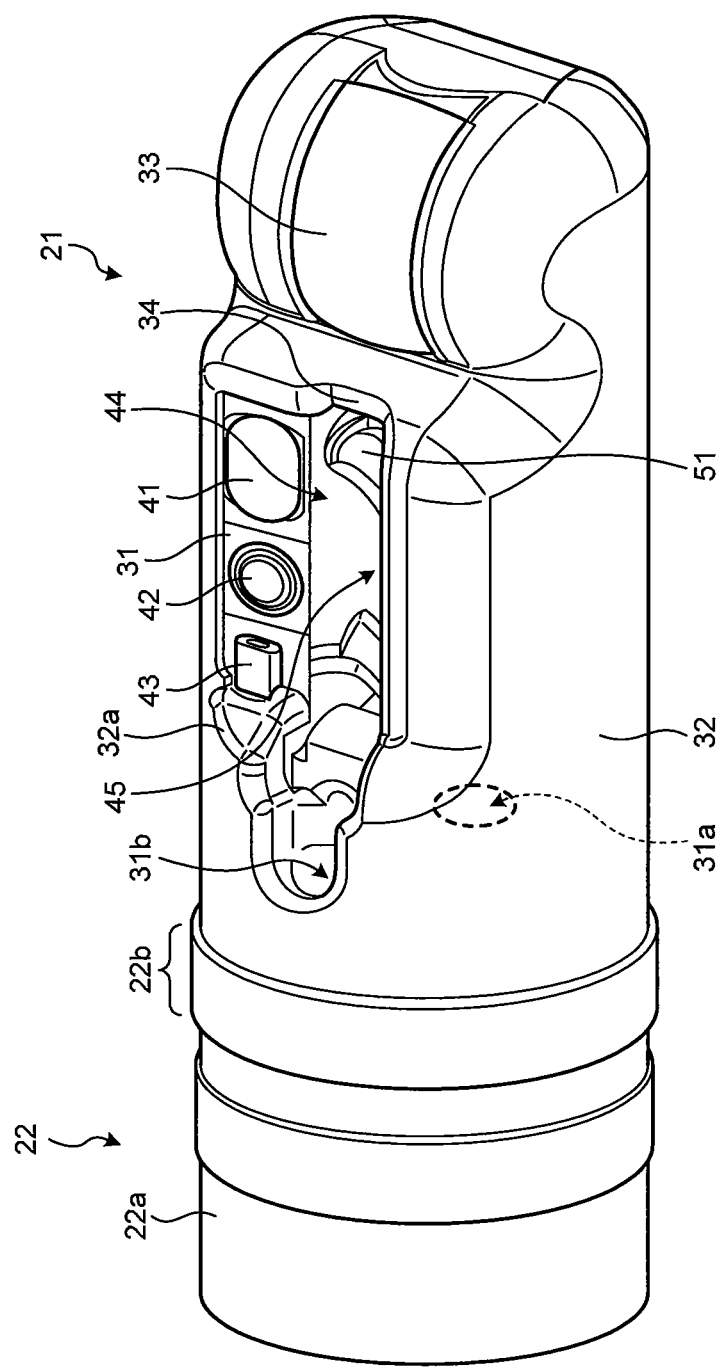
FIG. 8 is a perspective view illustrating a structure of a main portion of the endoscope system according to the embodiment of the present invention.
Figure 9:
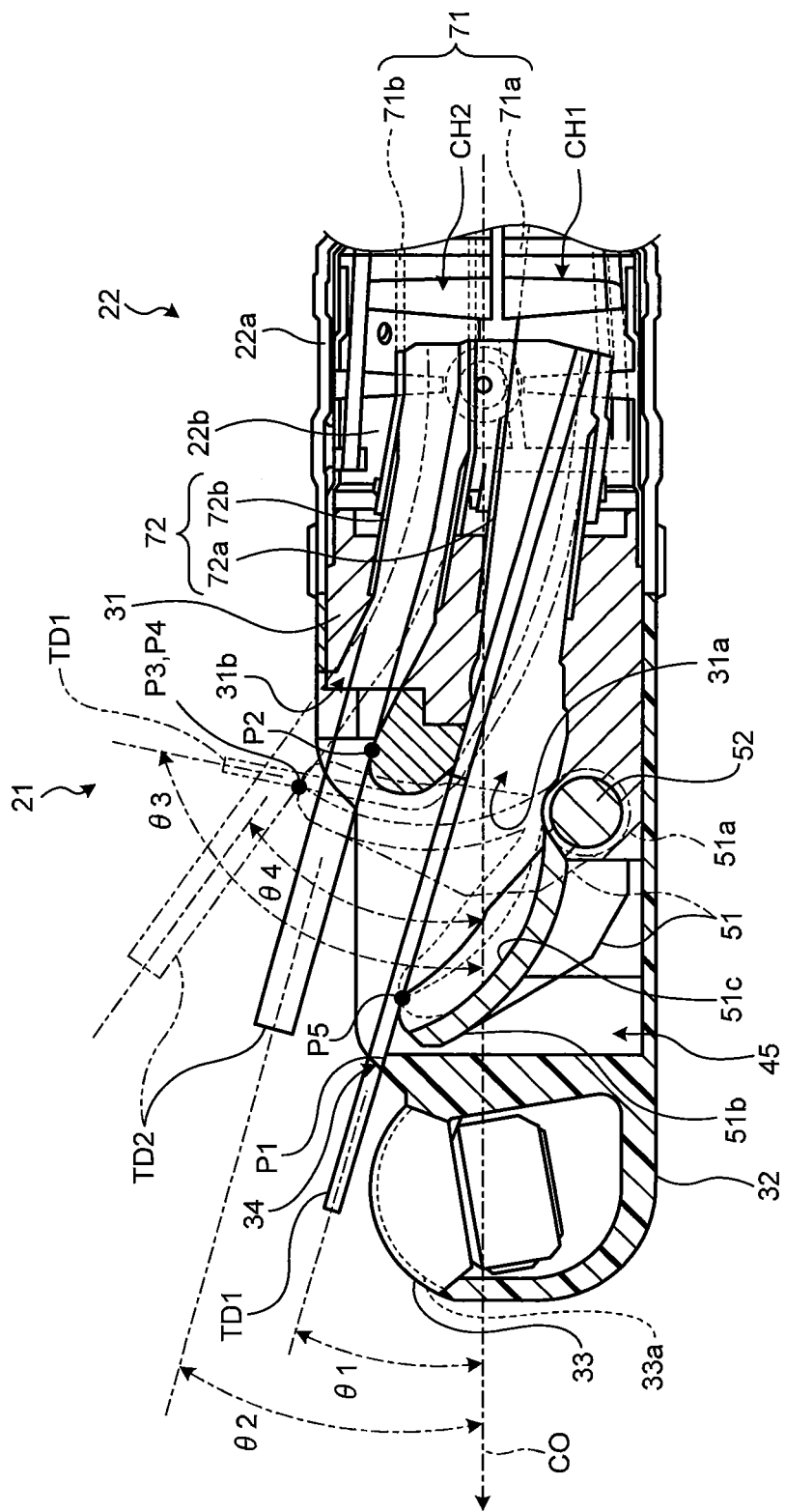
FIG. 9 is a cross-sectional view schematically illustrating the structure of the main portion of the endoscope system according to the embodiment of the present invention.

Reference will be made below to a structure of the distal end portion 21 of the inserting portion 11 in the endoscope 2. FIG. 8 is a perspective view illustrating a structure of a main portion of the endoscope system according to the embodiment of the present invention, and is the perspective view of the distal end portion 21 in a state that the raising base 51 is laid. FIG. 9 is a cross-sectional view schematically illustrating the structure of the main portion of the endoscope system according to the embodiment of the present invention, and is the cross-sectional view taken along a plane passing a center axis of the inserting portion 11 (insertion axis of the inserting portion 11) in the state illustrated in FIG. 8.

The distal end portion 21 is formed by including a metallic distal end hard member 31, and a cylindrical-shaped resin cover member 32 into which the distal end hard member 31 is inserted. In other words, the cover member 32 is attached to the distal end hard member 31 in a manner covering the same. With this configuration, insulation property of the distal end portion 21 can be surely obtained, and the ultrasound transducer unit can be surely fixed. The cover member 32 and the distal end hard member 31 are fixed by a bonding agent.

As illustrated in FIG. 8, a proximal end portion of the distal end portion 21 is covered with a curved rubber member 22a which is an outer coat of the curved portion 22. A proximal end portion of the cover member 32 and a distal end portion of the curved portion 22 are connected and fixed by a fixing tool such as a bobbin.

An ultrasound transducer unit 33 including an ultrasound transducer is housed inside a distal end portion of the cover member 32, and a cable of the ultrasound transducer unit 33 passes through a cable duct provided inside the cover member 32 and extends from an opening at the proximal end portion of the cover member 32. In other words, the cover member 32 integrates a cover that covers the distal end hard member 31 with a cover that covers the ultrasound transducer unit 33, and the cable of the ultrasound transducer unit 33 extends from the proximal end portion of the cover member 32. An outer diameter of the distal end portion 21 can be suppressed small by such a cover member 32.

As illustrated in FIG. 8, in a state that the cover member 32 is attached to the distal end hard member 31, a light window 41, an observation window 42, and a cleaning nozzle 43 are disposed in a manner aligned in an axial direction of the inserting portion 11 from a distal end side of the inserting portion 11 and exposed at an opening 32a of the cover member 32. The cleaning nozzle 43 is disposed such that water jetted from an opening of the cleaning nozzle 43 hits surfaces of the observation window 42 and light window 41.

In a state that the cover 32 is attached to the distal end hard member 31, a part of the opening 32a is covered by a part of the distal end hard member 31 where the light window 41, observation window 42, and cleaning nozzle 43 are disposed. A remaining portion of the opening 32a, which is not covered by a part of the distal end hard member 31 where the light window 41 and the like are disposed, constitutes an opening 44 from which the raising base 51 projects when the raising base 51 is raised.

At the distal end portion 21, a recessed portion 45 is formed in a direction from the opening 44 to the inside of the distal end hard member 31. The recessed portion 45 forms a space in which the raising base 51 is housed. As described later, when the raising base 51 is raised, a distal end portion of the raised portion 51 projects from the opening 44. In other words, the distal end portion 21 of the inserting portion 11 includes the recessed portion 45 formed on one side surface of the distal end portion 21 and capable housing the raising base 51.

A projecting portion 34 extending in a direction orthogonal to the insertion axis of the inserting portion 11 is formed between the ultrasound transducer unit 33 and the opening 44. The projecting portion 34 forms a contacting portion configured to come into contact with a side surface of a treatment tool TD1. According to the embodiment, a cannula, a puncture needle, a guide wire, and a stent are listed as the treatment tools, and the cannula is illustrated as an example of the treatment tool TD1 in FIG. 9.

Next, an inner structure of the distal end portion 21 will be described with reference to FIG. 9. The ultrasound transducer unit 33 is disposed at the distal end portion 21 of the inserting portion 11. The ultrasound transducer 33a inside the ultrasound transducer unit 33 is disposed at the distal end portion 21 of the inserting portion 11, and emits ultrasound waves to a side at a predetermined angle with respect to the insertion axis CO of the inserting portion 11.

As illustrated in FIG. 9, a proximal end portion of a distal end hard member 31 is fitted into a distal end portion of a curved piece 22b of the curved portion 22, and the curved piece 22b is fixed with the distal end hard member 31 by a fixing tool not illustrated. Two channel tubes 71 including channel tubes 71a and 71b are disposed inside the inserting portion 11. One of the two channel tubes 71 is the channel tube 71a for inserting a treatment tool such as the cannula to be used at the time of the ERCP, a stent and a forceps to be inserted at the time of expanding a stenosis portion, and constitutes a channel CH1 for the ERCP. The other one of the two channel tubes 71 is the channel tube 71b for inserting a treatment tool such as a puncture needle which is a puncture device used at the time of EUS-FNA, and constitutes a channel CH2 for the EUS-FNA.

The two channel tubes 71 are fixed to the distal end hard member 31 via pipe members 72 for fixation. A distal end portion of the channel tube 71a is fitted into a predetermined hole of the distal end hard member 31 and fixed by being externally inserted to an end portion of a pipe 72a, thereby connecting the channel tube 71a to the distal end hard member 31. In the same manner, a distal end portion of the channel tube 71b is fitted into another predetermined hole of the distal end hard member 31 and fixed by being externally inserted to an end portion of a pipe 72b, thereby connecting the channel tube 71b to the distal end hard member 31.

The channel CH1 formed by the channel tube 71a is in communication with an opening 31a provided on the distal end side of the distal end hard member 31. The channel CH2 formed by the channel tube 71b is in communication with an opening 31b provided on the distal end side of the distal end hard member 31.

As illustrated in FIG. 8, the opening 31a of the channel CH1 is formed on a bottom surface side of the inside of the recessed portion 45 distant from the opening 44. In other words, the opening 31a is disposed inside the recessed portion 45 of the distal end portion 21 of the inserting portion 11.

The opening 31b of the channel CH2 is located in the vicinity of the opening 44 of the inserting portion 11, disposed at a position different from the opening 31a, and formed at a position above and more distant from the bottom surface of the recessed portion 45 than the opening 31a. In other words, the two openings 31a and 31b of the two channels at the distal end portion 21 are aligned in order of the opening 31a and the opening 31b in a vertical direction from the bottom surface of the recessed portion 45 to the opening 44 at the time of viewing the inserting portion 11 from the distal end side, namely, in the direction from the bottom portion of the recessed portion 45 to the opening 44.

The raising base 51 is disposed inside the distal end hard member 31 in a manner rotatable around a predetermined axis. More specifically, an axial portion 52 which is a rotary axis member is fixed to the distal end hard member 31 in a manner rotatable around the axis, and the raising base 51 is axially supported by the axial portion 52 and disposed rotatably around a rotary axis of the axial portion 52. The axial portion 52 axially supports the raising base 51 at a proximal end portion 51a of the raising base 51.

The raising base 51 is a curved strip-shaped member formed in a direction from the proximal end portion 51a to a distal end portion 51b. The raising base 51 is disposed inside the distal end hard member 31 such that the distal end portion 51b of the raising base 51 is curved in a direction to the two openings 31a and 31b.

Further, the raising base 51 includes a contact surface 51c with which the treatment tool is configured to come into contact along the distal end portion 51b from the proximal end portion 51a on the two openings 31a and 31b sides. The contact surface 51c is a recessed portion forming a curved surface extending from the proximal end portion 51a to the distal end portion 51b.

Raising and laying operation for the raising base 51 is executed by operating the raising lever 29 at the operating unit 12. As described above, when the raising lever 29 is turned in a predetermined first direction (direction of arrow A1), the raising base 51 is raised and a part of the raising base 51 projects from the opening 44. In contrast, when the raising lever 29 is turned in a direction opposite to the first direction (direction of arrow A2), the raising base 51 is housed inside the recessed portion 45. Operation of the raising lever 29 is transmitted to the raising base 51 via a raising wire (not illustrated). When the raising wire moves back and forth inside the inserting portion 11 in accordance with operation of the raising lever 29, the raising base 51 integrally fixed to the axial portion 52 also rotates in accordance with the back and forth movement. A rotation range of the raising base 51 in a raising direction and a laying direction is controlled by a stopper not illustrated.

As described above, the raising base 51 is provided at the distal end portion 21 of the inserting portion 11, and is movable between a raised position approaching to the opening 31a and opening 31b and a laid position distant from the opening 31a and opening 31b by operating the raising lever 29.

As described above, the treatment tool is inserted from the respective forceps openings 25a and 25b provided at the channel opening setting portion 25 at the operating unit 12. The treatment tool for the EUS-FNA is inserted from the forceps opening 25a, and the treatment tool for the ERCP is inserted from the forceps opening 25b.

Next, functions of the endoscope 2 will be described with reference to FIGS. 9 to 11.

In FIG. 9, as indicated by a solid line, when the treatment tool TD1 such as the cannula is inserted into the channel CH1 from the forceps opening 25b when the raising base 51 is in a laid state, a distal end portion of the treatment tool TD1 passes through the inside of the channel CH1 and comes out from the opening 31a, and then contacts the contact surface 51c first. After that, the distal end portion of the treatment tool TD1 moves to the distal end portion 51b along the contact surface 51c. When the treatment tool TD1 is further pushed into the forceps opening 25b, the distal end portion of the treatment tool TD1 passes over the distal end portion 51b of the raising base 51, further passes over the projecting portion 34 between the opening 44 and the ultrasound transducer unit 33, and then projects from the opening 44.

At this point, the treatment tool TD1 projects from the opening 44 at an angle θ1 with respect to a distal end direction of the insertion axis CO of the inserting portion 11. The angle θ1 is defined by elasticity of the treatment tool TD1 itself, a position of the opening 31a, and a height of the projecting portion 34 which is the contacting portion. In the state illustrated in FIG. 9, a side surface of the treatment tool TD1 contacts a point P1 of the projecting portion 34. Therefore, the angle θ1 is substantially defined by the position of the treatment tool TD1 at the opening 31a and a position of the point P1.

Further, as indicated by the solid line in FIG. 9, when a treatment tool TD2 such as a puncture needle is inserted into the channel CH2 from the forceps opening 25a when the raising base 51 is in the laid state, a distal end portion of the treatment tool TD2 moves along an inner wall of the channel CH2. When the treatment tool TD2 is further pushed into the forceps opening 25a, the distal end portion of the treatment tool TD2 passes through the inside of the channel CH2 and comes out from the opening 31b, and then projects from the opening 44 without contacting the raising base 51.

At this point, the treatment tool TD2 projects from the opening 44 at an angle θ2 with respect to the distal end direction of the insertion axis CO of the inserting portion 11. The angle θ2 is defined by elasticity of the treatment tool TD2 itself, a position of the opening 31b, and an inner wall shape of the channel CH2 in the vicinity of the opening 31b. In the case of FIG. 9, a side surface of the treatment tool TD2 contacts a point P2 of the opening 31b. Therefore, the angle θ2 is substantially defined by the position of the treatment tool TD2 at the opening 31a and a position of the point P2.

In this case, the treatment tool TD1 projects forward at the angle θ1 with respect to the distal end direction of the insertion axis CO, and the angle θ1 is defined by the elasticity of the treatment tool TD1 itself, the position of the opening 31a, and the height of the projecting portion 34.

However, the height of the projecting portion 34 may be decreased such that the treatment tool TD1 contacts the distal end portion 51b of the raising base 51, or a height of the distal end portion 51b from the bottom surface of the recessed portion 45 may be increased when the raising base 51 is laid. In such a case, the angle θ1 is defined by the elasticity of the treatment tool TD1 itself, the position of the opening 31a, and the height of the distal end portion 51b, and the treatment tool TD1 does not contact the ultrasound transducer unit 33.

In this case, the side surface of the treatment tool TD1 does not contact the projecting portion 34 in FIG. 9, and the side surface of the treatment tool TD1 contacts the raising base 51 at a point P5 at the distal end portion 51b of the raising base 51 indicated by a dotted line.

In other words, when the raising base 51 is in the laid position, the laid the raising base 51 may be formed such that the side surface of the treatment tool TD1 does not contact the surface of the ultrasound transducer unit 33 including the ultrasound transducer 33a and the treatment tool TD1 projects from the opening 31a.

In FIG. 9, as indicated by an alternate long and two short dashed line, when the raising base 51 is in a raised state, projecting directions of the treatment tools TD1, TD2 are changed by the raising base 51.

When executing raising operation by the raising lever 29 after the distal end portion of the treatment tool TD1 passes through the inside of the channel CH1 and comes out from the opening 31a, the raising base 51 is raised as indicated by the alternate long and two short dashed line in FIG. 9 and the projecting direction of the distal end portion of the treatment tool TD1 is changed. FIG. 9 illustrates a state in which the raising base 51 indicated by the alternate long and two short dashed line is raised highest. A maximum raised angle of the treatment tool TD1 is an angle θ3 with respect to the distal end direction of the insertion axis CO of the distal end portion 21. The angle θ3 is defined by the elasticity of the treatment tool TD1 itself, a shape of the opening 31a, and a shape of the distal end portion 51b of the raising base 51. In the case of FIG. 9, the side surface of the treatment tool TD1 contacts the point P3 at the distal end portion 51b of the raising base 51. Therefore, the angle θ3 is substantially defined by the position of the treatment tool TD1 at the opening 31a and the position of the point P3.

When executing the raising operation by the raising lever 29 after the distal end portion of the treatment tool TD2 such as the puncture needle passes through the inside of the channel CH2 and comes out of the opening 31b, the raising base 51 is raised as indicated by the alternate long and two short dashed line in FIG. 9, and the projecting direction of the distal end portion of the treatment tool TD2 is changed. A maximum raised angle of the treatment tool TD2 is an angle θ4 with respect to the distal end direction of the insertion axis CO of the distal end portion 21. The angle θ4 is defined by the elasticity of the treatment tool TD2 itself, the position of the opening 31b, the inner wall shape of the channel CH2 in the vicinity of the opening 31b, and a shape of the distal end portion 51b of the raising base 51. In the case of FIG. 9, the side surface of the treatment tool TD2 contacts a point P4 at the opening 31b. Therefore, the angle θ4 is substantially defined by the position of the treatment tool TD2 at the opening 31b and a position of the point P4. Note that the point P3 and the point P4 are indicated at the same position in FIG. 9, but strictly, the positions of the point P3 and point P4 are different.

Here, the angle θ1 is 5 degrees or more and 40 degrees or less, preferably, from 10 to 15 degrees. The angle θ2 is 10 degrees or more and 40 degrees or less, preferably, from 15 to 20 degrees.

The angle θ3 is 90 degrees or more and 130 degrees or less, preferably, from 100 to 110 degrees. The angle θ4 is 10 degrees or more and 40 degrees or less, preferably, from 30 to 35 degrees.

As described above, the raising base 51 is disposed at the distal end portion 21, and contacts the treatment tool TD1 projecting from the opening 31a at the point P3, and allows the treatment tool TD1 to extend in the direction of the angle θ3. Further, the raising base 51 contacts the treatment tool TD2 projecting from the opening 31b at the point P4, and allows the treatment tool TD2 to extend in the direction of the angle θ4 different from the direction of the angle θ3.

Particularly, in the above example, in the case where the raising base 51 is in the raised position and the treatment tool TD1 projects from the opening 31a, the side surface of the treatment tool TD1 contacts the raising base 51 at the point P3. Further, in the case where the raising base 51 is in the raised position and the treatment tool TD2 projects from the opening 31b, the side surface of the treatment tool TD2 contacts the raising base 51 at the point P4. Additionally, the contact portion of the point P3 and the contact portion of the point P4 at the raising base 51 are substantially same at an end portion of the raising base 51.

Figure 10:
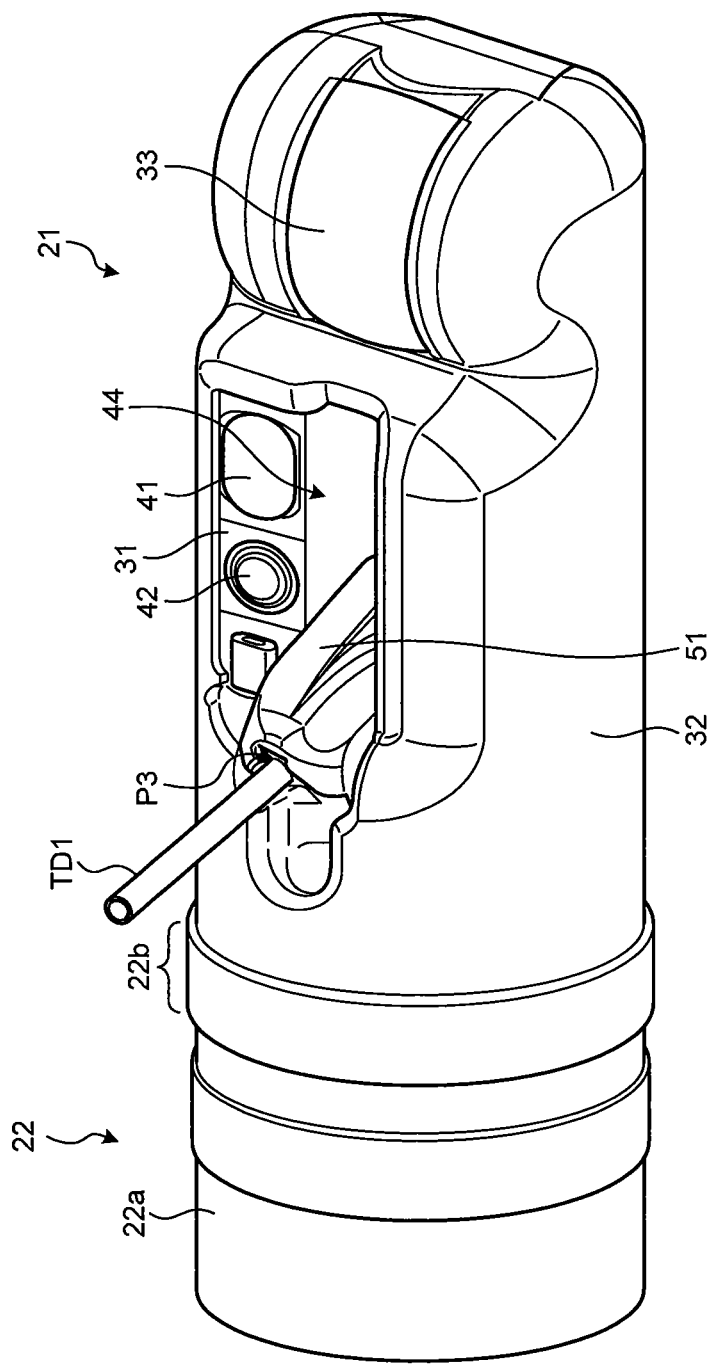
FIG. 10 is a perspective view illustrating the structure of the main portion of the endoscope system according to the embodiment of the present invention.
Figure 11:
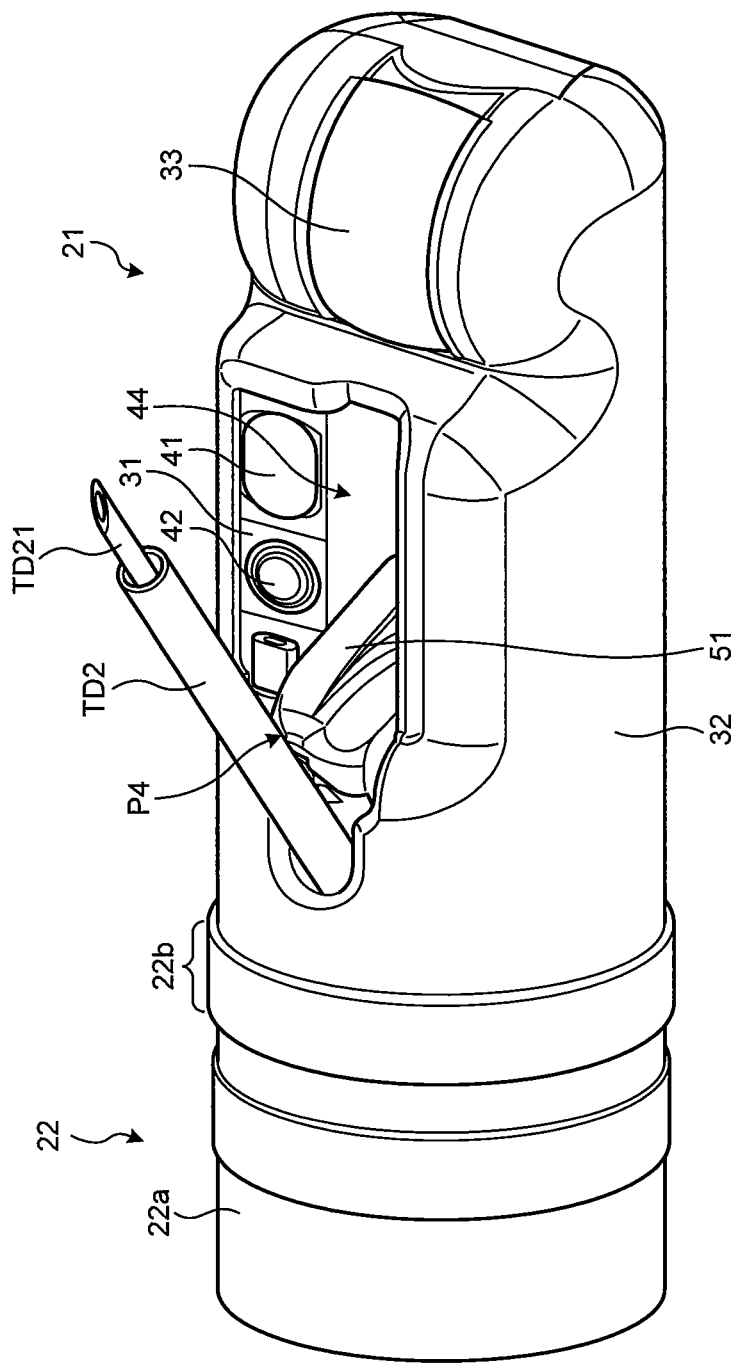
FIG. 11 is a perspective view illustrating the structure of the main portion of the endoscope system according to the embodiment of the present invention.

FIG. 10 is a perspective view schematically illustrating a structure of the main portion of the endoscope system according to the embodiment of the present invention, and is the perspective view illustrating the distal end portion 21 in a state that the distal end portion of the treatment tool TD1 projects from the opening 44 when the raising base 51 is in a most raised state. FIG. 11 is a perspective view schematically illustrating the structure of the main portion of the endoscope system according to the embodiment of the present invention, and is the perspective view illustrating the distal end portion 21 in a state that the distal end portion of the treatment tool TD2 projects from the opening 44 when the raising base 51 is in the most raised state. In FIG. 11, the treatment tool TD2 is the puncture needle, and a needle tube TD21 projects.

For example, in the case where the operator inserts the inserting portion 11 of the endoscope 2 into a stomach and executes biopsy of a pancreas while observing an ultrasound image, the biopsy can be executed through a wall of the stomach by using the treatment tool TD2, namely, the puncture needle by operating the raising lever 29. Further, in the case where a lesion site is found at a head of the pancreas, a bile duct or the like from the ultrasound image and it is determined that the ERCP is needed, the treatment tool TD1 is inserted from the forceps opening 25b instead of the treatment tool TD2 without pulling out the endoscope 2, and the ERCP can be performed by operating the raising lever 29 to insert the cannula or the like from a papilla portion.

Next, a procedure at the time of inserting a stent into a stenosis portion inside the biliary tract of the subject by using the above-described ultrasound endoscope system 1 will be described with reference to FIGS. 12 to 19. FIGS. 12 to 19 are explanatory diagrams for a method of inserting a treatment tool by using the endoscope system according to the embodiment of the present invention.

Figure 12:
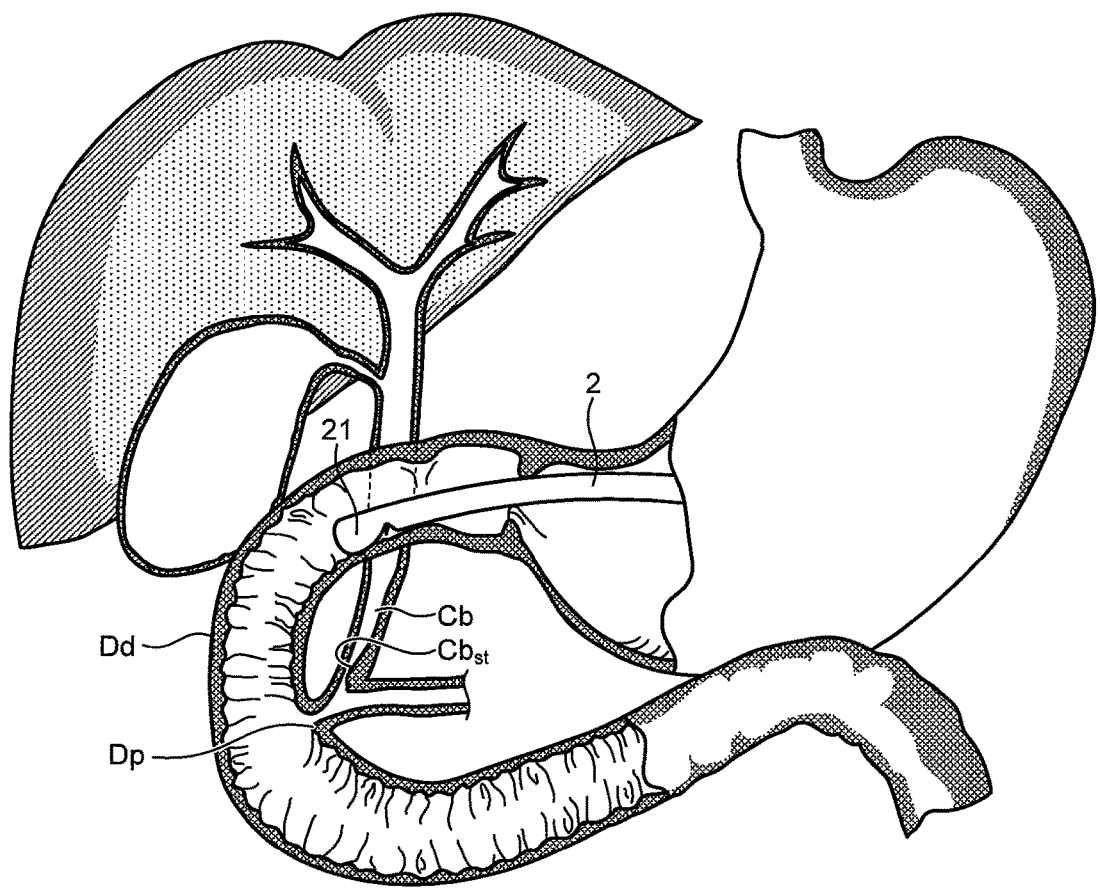
FIG. 12 is an explanatory diagram for a method of inserting a treatment tool by using the endoscope system according to an embodiment of the present invention.
Figure 13:
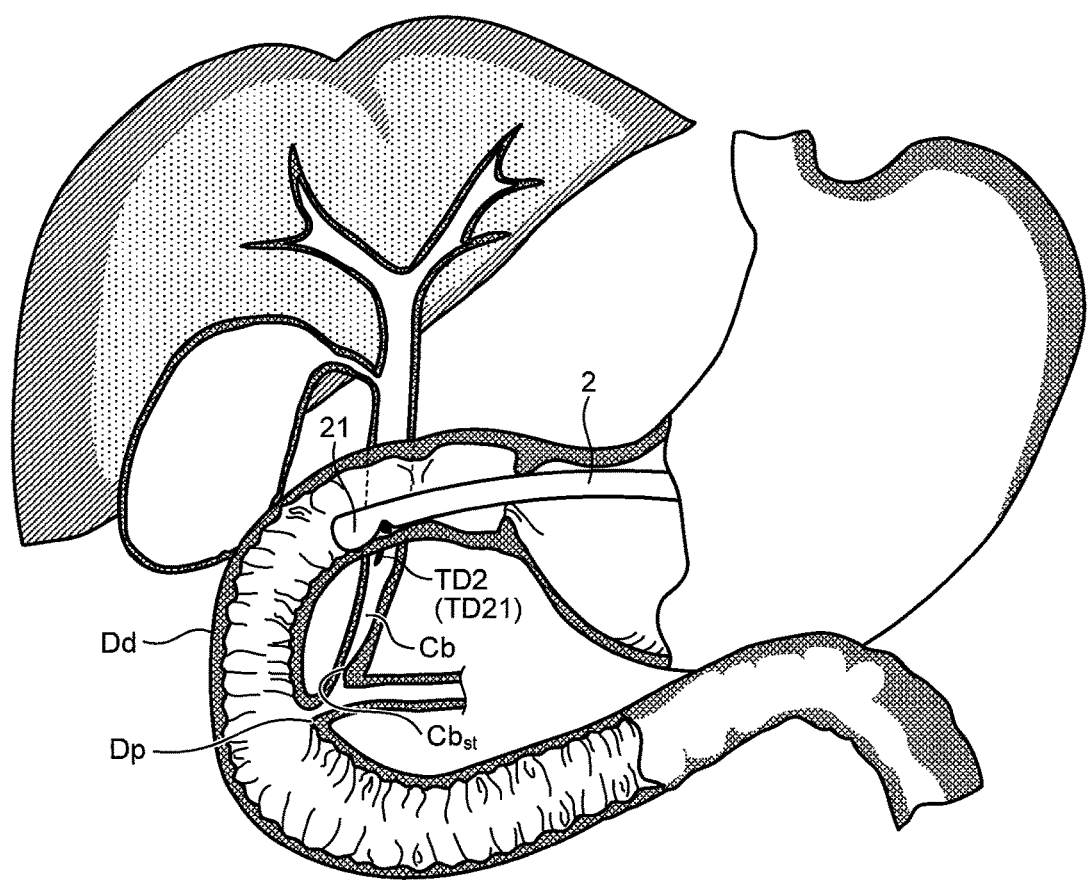
FIG. 13 is an explanatory diagram for the method of inserting a treatment tool by using the endoscope system according to the embodiment of the present invention.

First, the operator inserts the distal end portion 21 of the inserting portion 11 into the subject up to a duodenum Dd while observing a captured image displayed on the monitor 5 as illustrated in FIG. 12. After that, the treatment tool TD2 which is the puncture needle is inserted into the channel CH2 while observing an ultrasound image displayed on the monitor 7, and the needle tube TD21 is made to project from the opening 44, and then the common bile duct Cb where the stenosis portion $Cb_{st}$ is formed is punctured with the needle tube TD21 from the duodenum Dd (refer to FIG. 13). At this point, the raised angle of the needle tube TD21 is preferably 20 degrees or more and 40 degrees or less in the viewpoint that puncturing the common bile duct Cb can be easily performed from the duodenum Dd. The endoscopic ultrasound-guided fine needle aspiration (FNA) can be performed by the above-described procedure.

Figure 14:
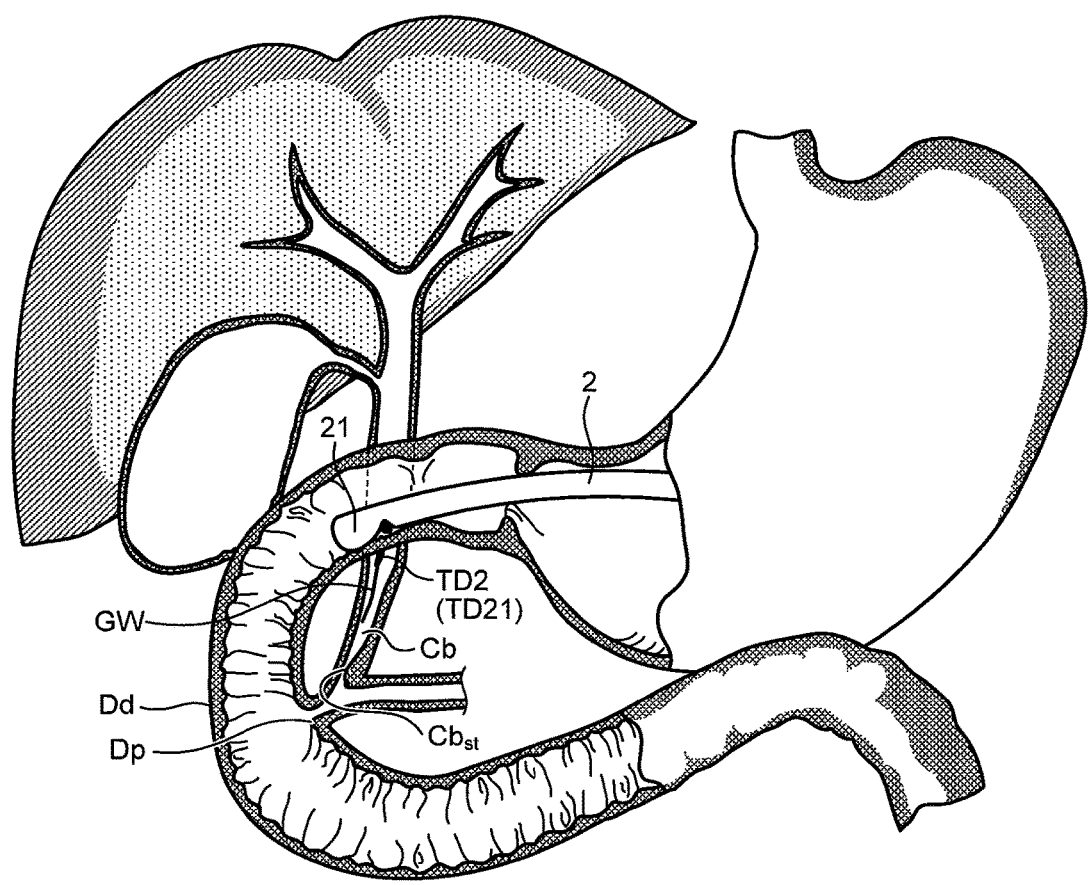
FIG. 14 is an explanatory diagram for the method of inserting a treatment tool by using the endoscope system according to the embodiment of the present invention.
Figure 15:
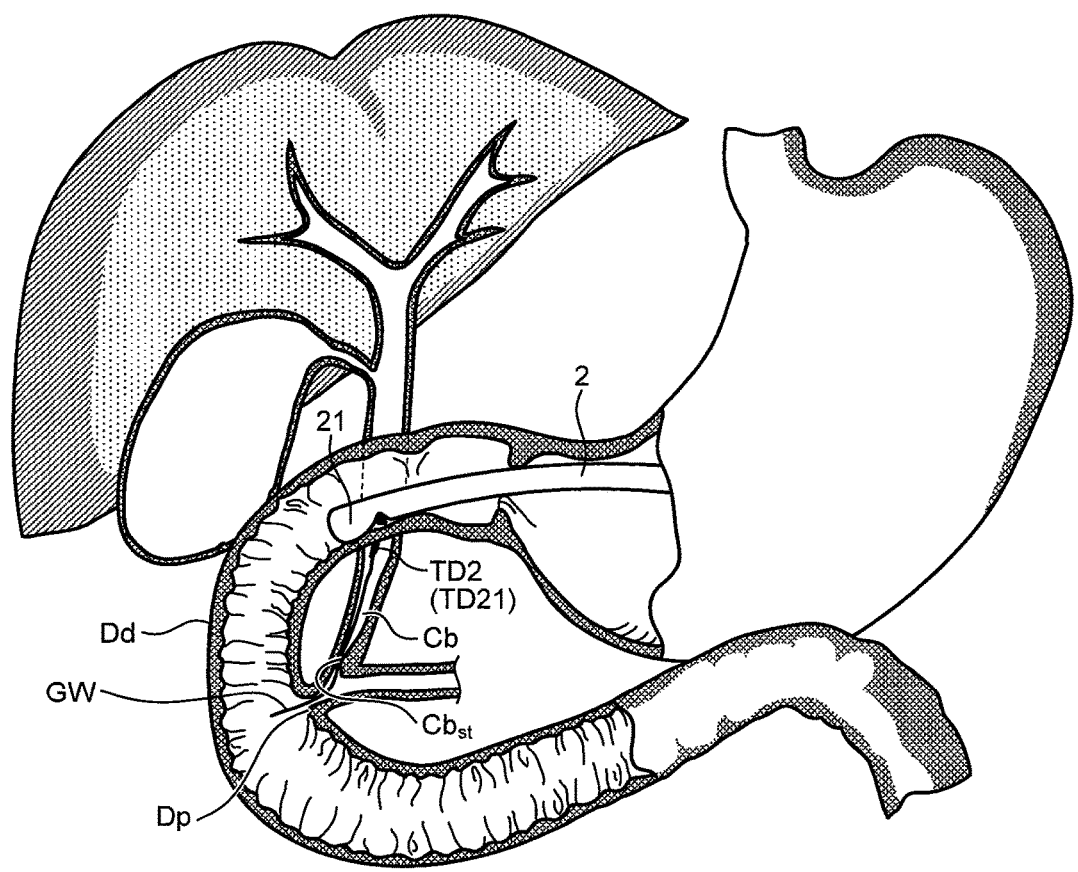
FIG. 15 is an explanatory diagram for the method of inserting a treatment tool, using the endoscope system according to the embodiment of the present invention.

After that, a contrast agent is injected into the common bile duct Cb via the needle tube TD21 of the treatment tool TD2, and a guide wire GW is inserted into the common bile duct Cb via the needle tube TD21 while performing radiographic visualization and observing the common bile duct Cb (refer to FIG. 14). After inserting the guide wire GW into the common bile duct Cb, the guide GW wire is further fed into the common bile duct Cb, and the distal end of the guide wire GW is placed inside the duodenum Dd via the duodenal papilla Dp (refer to FIG. 15). At this point, an extending amount of the guide wire GW from the duodenal papilla Dp is a length corresponding to a later-described moving amount of the distal end portion 21 or more. The extending amount of the guide wire GW from the duodenal papilla Dp can be confirmed by radiography and the like.

Figure 16:
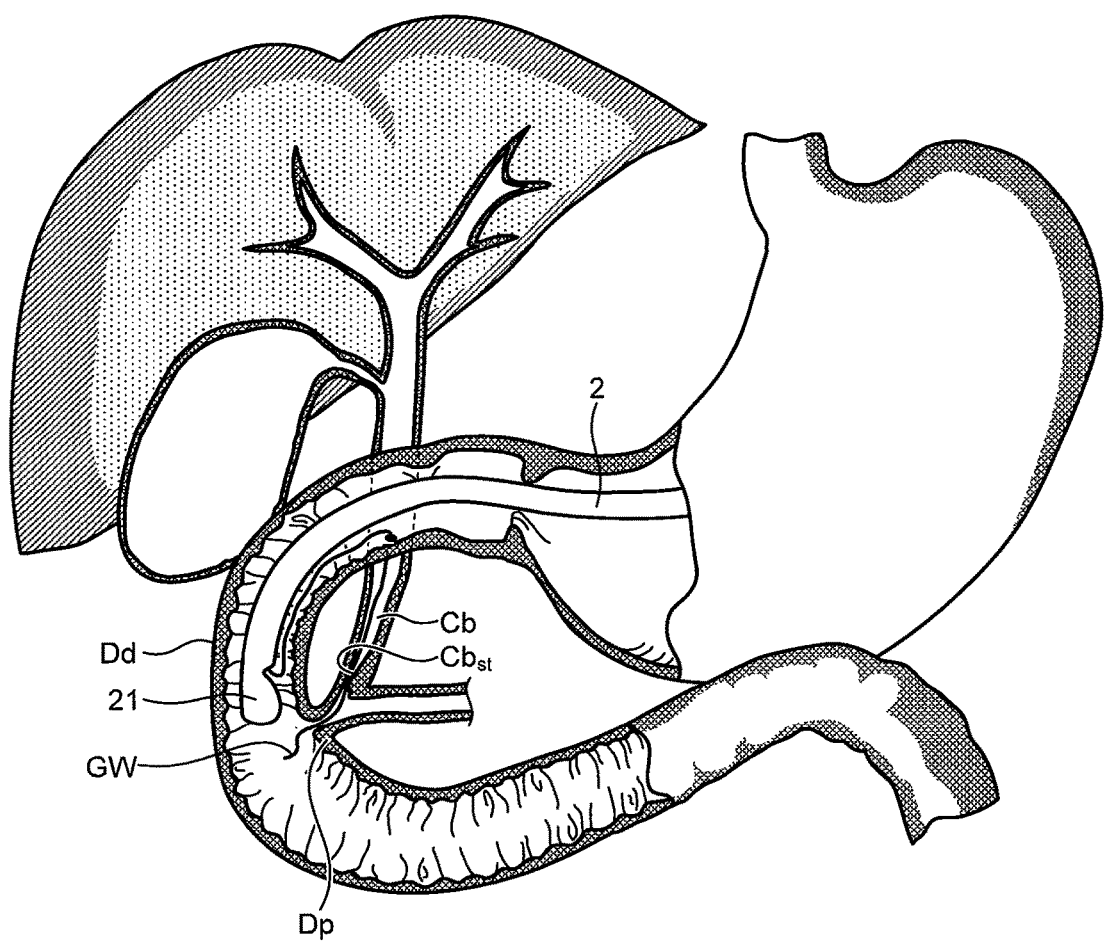
FIG. 16 is an explanatory diagram for the method of inserting a treatment tool by using the endoscope system according to the embodiment of the present invention.

After the distal end of the guide wire GW is placed inside the duodenum Dd, the treatment tool TD2 (puncture needle) is retracted from the distal end portion 21 while leaving the guide wire GW, and then the distal end portion 21 is moved up to the duodenal papilla Dp while observing the captured image (refer to FIG. 16). The extending amount of the above-described guide wire GW from the duodenal papilla Dp is only needed to be an extent that the guide wire GW pulled toward the common bile duct Cb side due to the above-mentioned movement of the distal end portion 21 extends from the duodenal papilla Dp to the duodenum Dd side.

Figure 17:
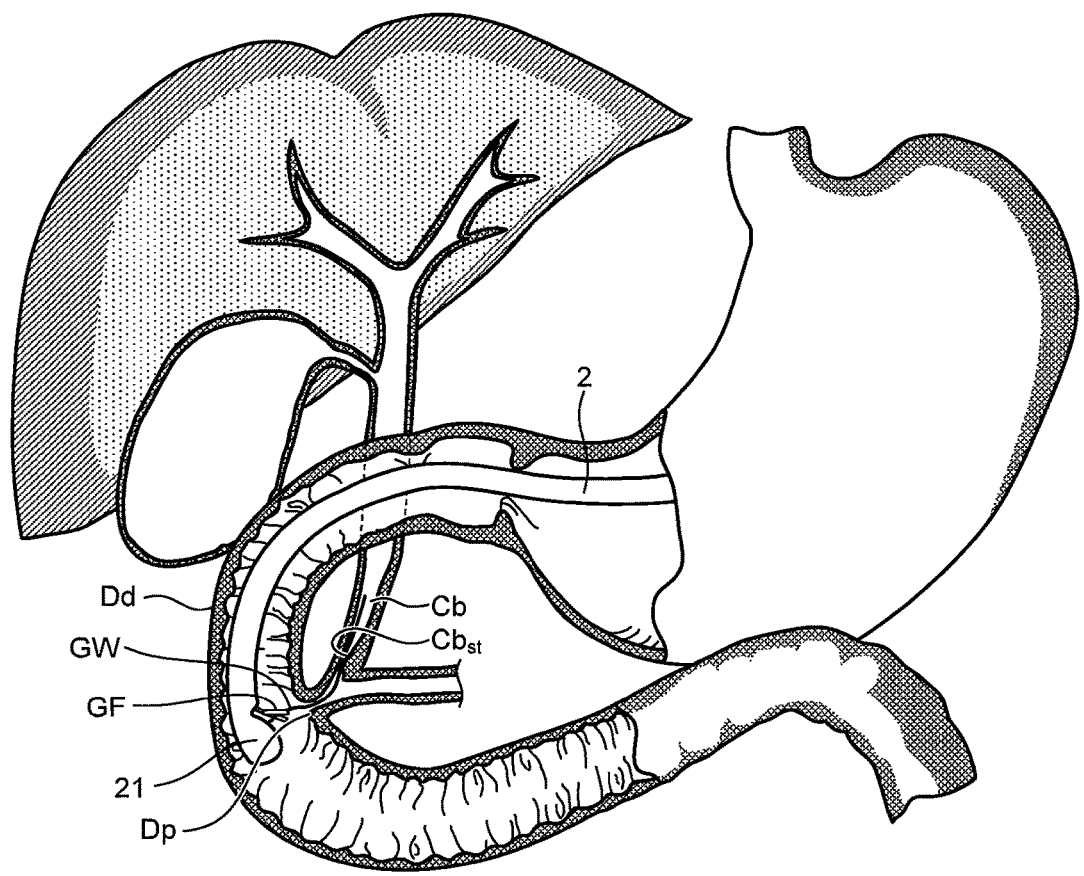
FIG. 17 is an explanatory diagram for the method of inserting a treatment tool by using the endoscope system according to the embodiment of the present invention.
Figure 18:
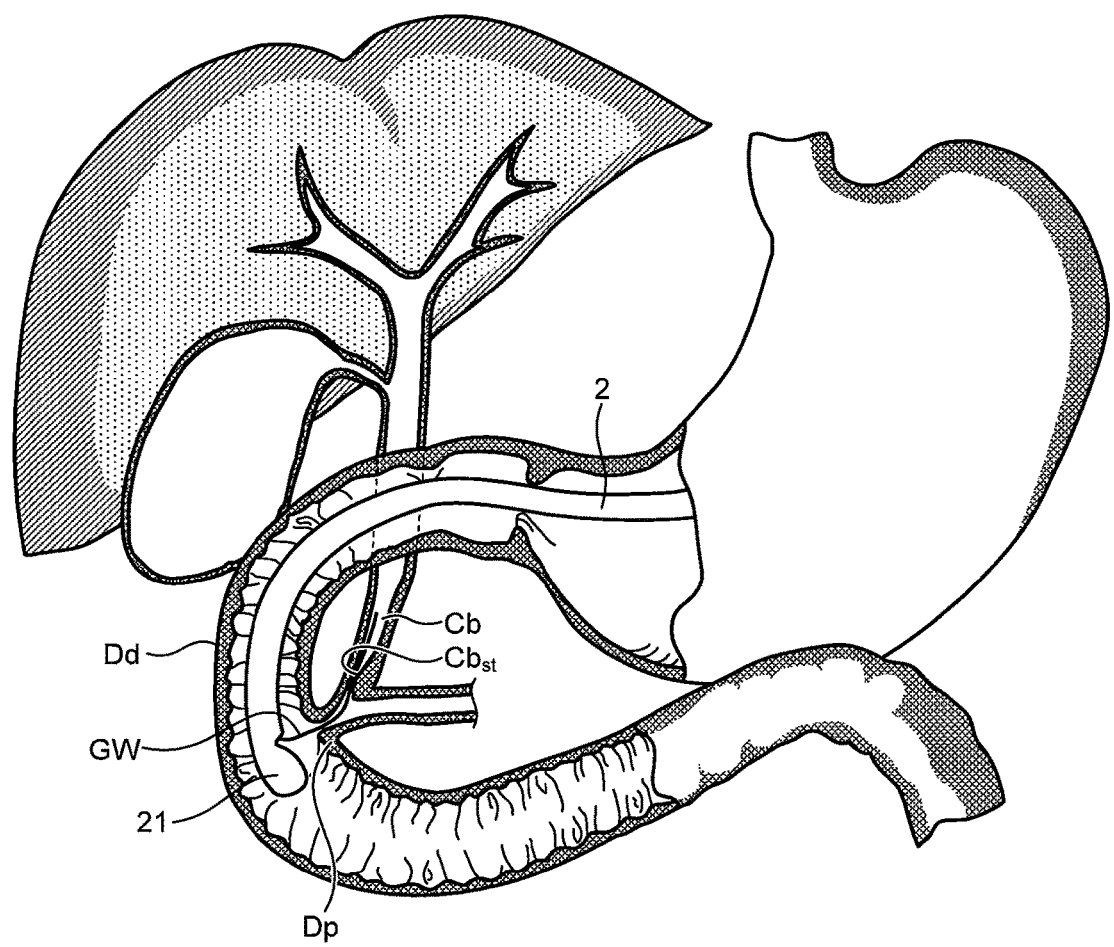
FIG. 18 is an explanatory diagram for the method of inserting a treatment tool by using the endoscope system according to the embodiment of the present invention.

After moving the distal end portion 21 up to the duodenal papilla Dp, a gripping forceps GF as the treatment tool TD1 is inserted into the channel CH1 and made to extend from the opening 44, and the distal end of the guide wire GW extending from the duodenal papilla Dp is gripped by the gripping forceps GF (refer to FIG. 17). Subsequently, the gripping forceps GF is pulled out from the channel CH1, and the guide wire GW extending from the duodenal papilla Dp is pulled into the inserting portion 11 (refer to FIG. 18). At this point, the guide wire GW is pulled into the channel CH1 until the end portion of the guide wire GW which is opposite to the side gripped by the gripping forceps GF is located inside the common bile duct Cb. With this, the guide wire GW extends from the distal end portion 21, and the side from where the end portion of the guide wire GW extends is placed inside the common bile duct Cb.

Figure 19:
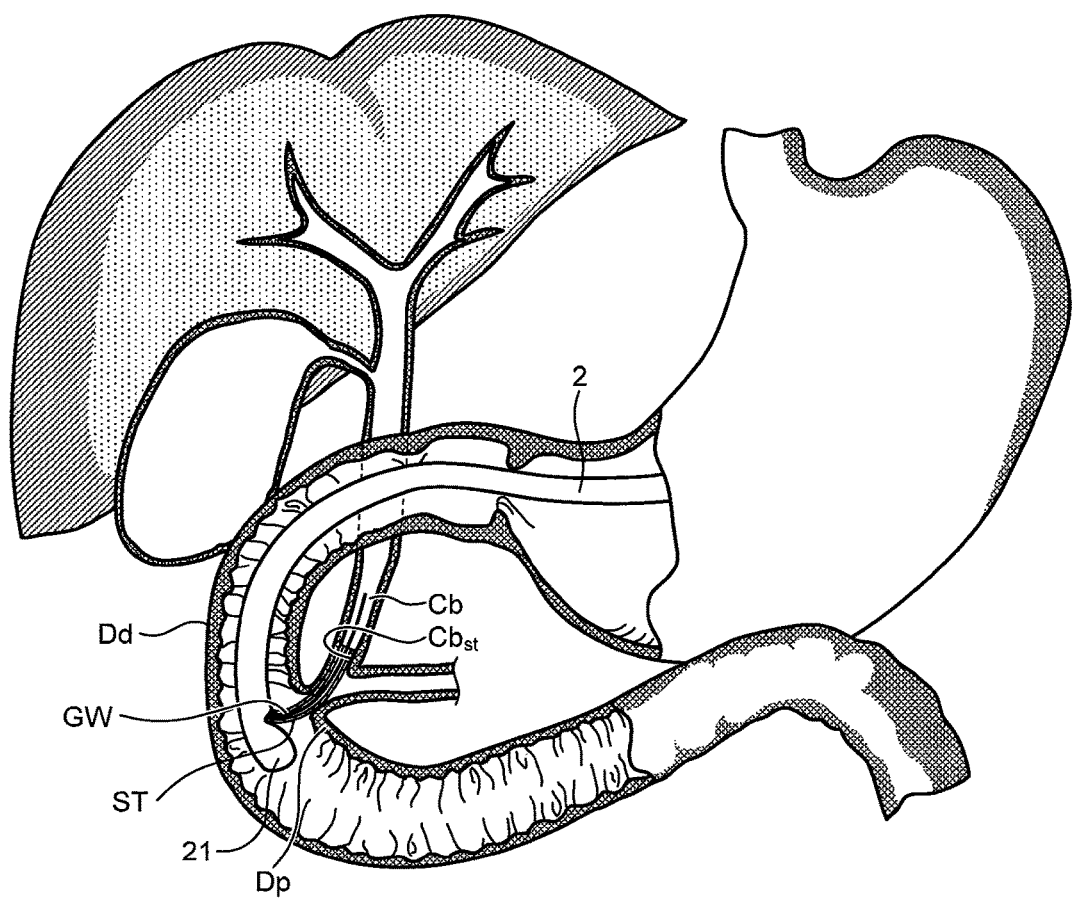
FIG. 19 is an explanatory diagram for the method of inserting a treatment tool by using the endoscope system according to the embodiment of the present invention.

In this state, the cylindrical-shaped stent ST as the treatment tool TD1 is inserted into the channel CH1 via the guide wire GW, the stent ST is placed in the duodenal papilla Dp and the stenosis portion $Cb_{st}$ by feeding the stent ST along the guide wire GW, thereby achieving to expand the stenosis portion $Cb_{st}$ by the stent ST (refer to FIG. 19). At this point, the raised angles of the gripping forceps GF and the stent ST by the raising base 51 are preferably 60 degrees or more and 120 degrees or less in the viewpoint that the guide wire GW can be easily gripped and the stent ST can be easily inserted from the duodenal papilla Dp to the common bile duct Cb. In the case where the common bile duct Cb is hardly viewable by radiographic observation at the time of inserting the stent ST, the cannula may be inserted into the duodenal papilla Dp via the guide wire GW and the contrast agent is injected again to the common bile duct Cb. When the stent ST is inserted into the duodenal papilla Dp, the duodenal papilla Dp is expanded by a known method such as a balloon and a dilator, and the stent ST is inserted into the expanded duodenal papilla Dp. By inserting the stent ST into the stenosis portion $Cb_{st}$, treatment inside the biliary tract including the common bile duct Cb can be performed via the stent ST.

According to the above-described embodiment, operation of the guide wire GW and insertion of the stent ST into the stenosis portion $Cb_{st}$ are performed by performing puncturing with the needle tube TD21 from the channel CH2 while observing the ultrasound image, and making the guide wire GW extend from the duodenal papilla Dp into the duodenum Dd via the common bile duct Cb by using the endoscope 2 including the two channels (channels CH1 and CH2) from which the treatment tool can be extended at different angles, and then extending the gripping forceps GF and the stent ST from the channel CH1 at the raised angle larger than the channel CH2. Therefore, the stent ST can be inserted into the stenosis portion $Cb_{st}$ of the common bile duct Cb without replacing the scope. By this, the above-described method of inserting a treatment tool can be more easily performed in a reduced time. Further, compared to the method of inserting a treatment tool in the related art, the number of scopes and the number of operators required to perform the procedure can be reduced. As a result, the cost needed for the procedure can be reduced.

Modified Example of Embodiment

According to the above-described embodiment, the guide wire GW is kept extending from the duodenal papilla Dp by adjusting the extending amount of the guide wire GW from the duodenal papilla Dp even when the distal end portion 21 is moved, but not limited thereto. For example, the guide wire GW may be fed into the inserting portion 11 along with the movement of the distal end portion 21, and a predetermined amount of the guide wire GW may be made to extend between the duodenum Dd and the distal end portion 21 inside the duodenum Dd.

Figure 20:
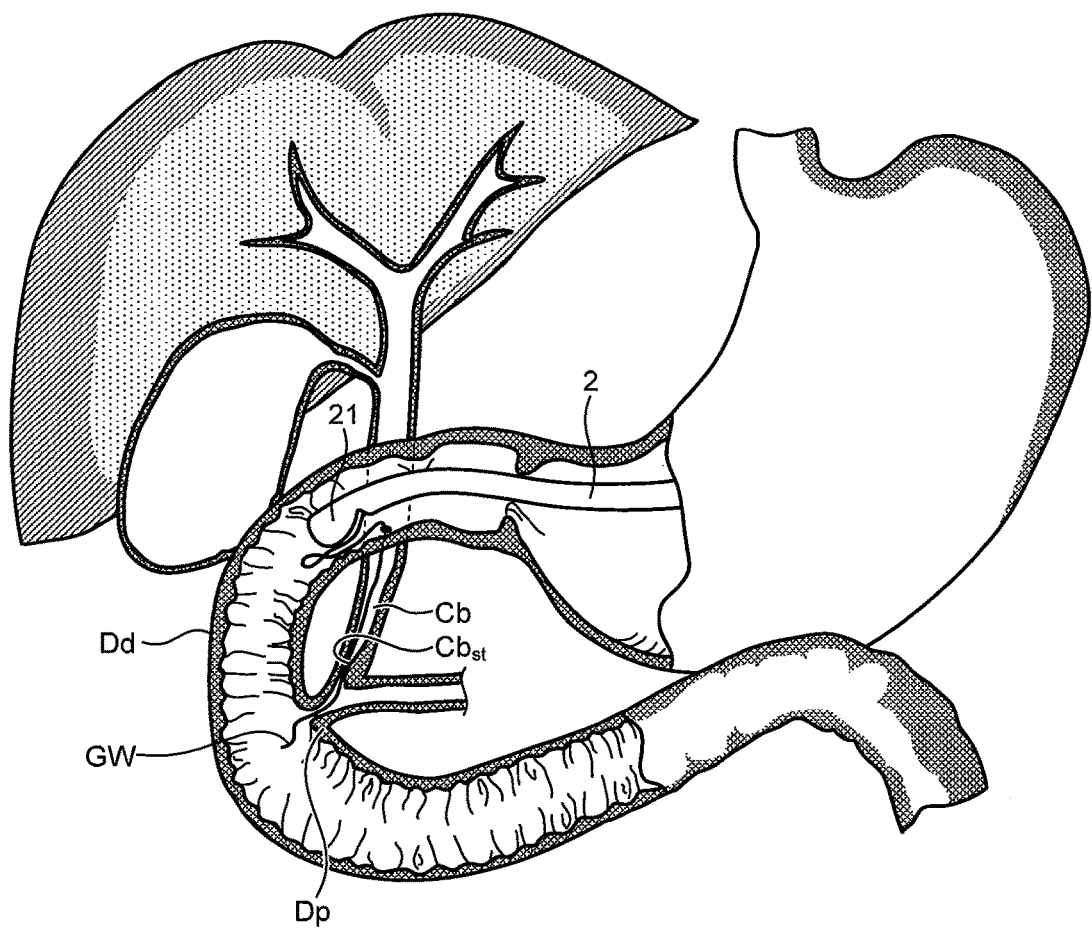
FIG. 20 is an explanatory diagram for a method of inserting a treatment tool by using the endoscope system according to a modified example of the embodiment of the present invention.

FIG. 20 is an explanatory diagram for a method of inserting a treatment tool using the endoscope system according to a modified example of the embodiment of the present invention, and is the explanatory diagram for operation of the guide wire GW. As illustrated in FIG. 20, the predetermined amount of the guide wire GW is extended inside the duodenum Dd. By this, even when the distal end portion 21 is moved, the extending amount of the guide wire GW extending from the duodenal papilla Dp can be prevented from being changed, and further the guide wire GW is prevented from being pulled toward the distal end portion 21 side at a puncturing portion of the duodenal papilla Dp and the duodenum Dd.

According to the above-described embodiment, the end portion of the guide wire GW which is opposite to the side gripped by the gripping forceps GF is placed inside the common bile duct Cb, but the mentioned end portion may be placed inside the duodenum Dd, or may be placed inside the endoscope 2 (inserting portion 11).

Further, according to the above-described embodiment, the stent ST is placed in the duodenal papilla Dp and the stenosis portion $Cb_{st}$, but the stent ST is only needed to be placed in the stenosis portion $Cb_{st}$. Additionally, the above-described procedure is not limited to the stent ST, and may be applicable to any treatment tool that is inserted into the biliary tract.

Further, according to the above-described embodiment, the common bile duct Cb is punctured with the puncture needle from the duodenum Dd, but other biliary tracts including the intrahepatic bile duct and the gallbladder may also be punctured with the puncture needle, besides the common bile duct Cb. In other words, the guide wire GW only has to access the common bile duct Cb and the duodenal papilla Dp via some biliary tract.

Figure 21:
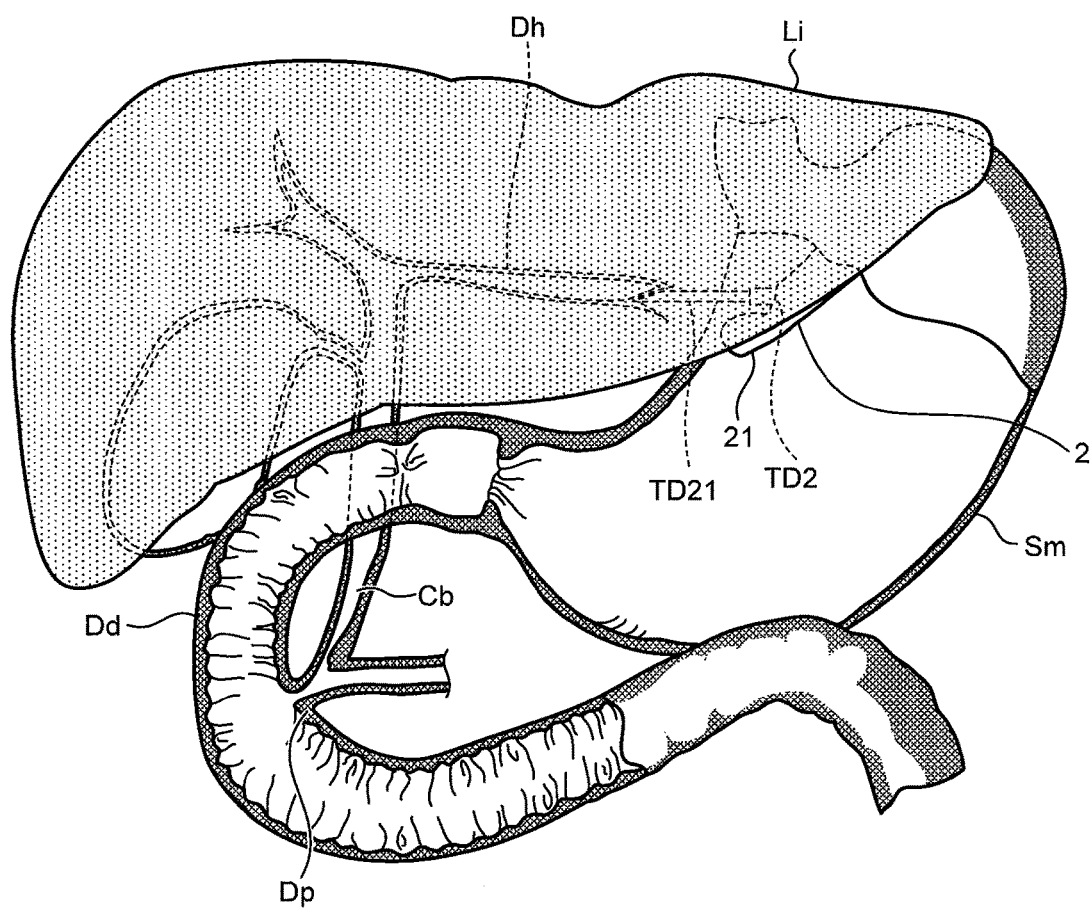
FIG. 21 is an explanatory diagram for a method of inserting a treatment tool by using the endoscope system according to another example of the embodiment of the present invention.

Further, according to the above-described embodiment, the common bile duct Cb (biliary tract) is punctured with the puncture needle from the duodenum Dd, but the biliary tract may be punctured from an upper digestive tract such as the stomach with the puncture needle as well, besides the duodenum Dd. FIG. 21 an explanatory diagram for a method of inserting a treatment tool using the endoscope system according to another example of the embodiment. As illustrated in FIG. 21, the treatment tool TD2 may project inside the stomach Sm in the vicinity of the liver Li, and a wall surface of the stomach Sm may be punctured with the needle tube TD21 to access the left hepatic duct Dh.

The present invention is not limited to the above-described embodiments and modified examples, and may include various embodiments in a range not departing from the technical idea described in the claims. In addition, the embodiments and modified examples may be combined together appropriately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of inserting a treatment tool, comprising:
   making a puncture needle project from a first channel of an endoscope at a first raised angle with respect to a longitudinal axis of the endoscope and puncturing an upper digestive tract to place a distal end of a needle tube of the puncture needle inside a biliary tract while observing an ultrasound image;
   inserting a guide wire into the biliary tract via the needle tube and making a distal end of the guide wire extend out from a duodenal papilla into a duodenum;
   placing a distal end portion of the endoscope in vicinity of the duodenal papilla while keeping the distal end of the guide wire extending out from the duodenal papilla while observing a captured image;
   pulling a first end portion of the guide wire extending out from the duodenal papilla into a second channel of the endoscope at a second raised angle with respect to the longitudinal axis of the endoscope, the second raised angle being larger than the first raised angle; and
   inserting the treatment tool inside the biliary tract via the guide wire.

2. The method of inserting the treatment tool according to claim 1, wherein
   the treatment tool is cylindrical-shaped, and
   inserting the cylindrical-shaped treatment tool inside the biliary tract includes inserting the cylindrical-shaped treatment tool at least up to a position of the biliary tract including a stenosis portion.

3. The method of inserting the treatment tool according to claim 1, wherein making the distal end of the guide wire extend out from the duodenal papilla into the duodenum includes making the guide wire extend until an extending amount of the guide wire from the duodenal papilla becomes equal to or more than a moving amount of the distal end portion of the endoscope to move from a position punctured with the puncture needle to the duodenal papilla.

4. The method of inserting the treatment tool according to claim 1, wherein making the distal end of the guide wire extend out from the duodenal papilla into the duodenum includes making the guide wire extend until an extending amount of the guide wire extending from the distal end portion of the endoscope into the duodenum becomes equal to or more than a moving amount of the distal end portion of the endoscope.

5. The method of inserting the treatment tool according to claim 1, wherein pulling the first end portion of the guide wire into the second channel includes pulling the first end portion of the guide wire until a second end portion of the guide wire which is opposite to the first end portion is placed inside the biliary tract.

6. The method of inserting the treatment tool according to claim 1, wherein pulling the first end portion of the guide wire into the second channel includes pulling the first end portion of the guide wire until a second end portion of the guide wire which is opposite to the first end portion is placed inside the upper digestive tract.

7. The method of inserting the treatment tool according to claim 1, wherein pulling the first end portion of the guide wire into the second channel includes pulling the first end portion of the guide wire until a second end portion of the guide wire which is opposite to the first end portion is placed inside the endoscope.

8. The method of inserting the treatment tool according to claim 1, wherein
   the first raised angle is 20 to 40 degrees; and
   the second raised angle is 60 to 120 degrees.

9. The method of inserting the treatment tool according to claim 1, wherein the endoscope includes an ultrasound transducer unit at the distal end portion.

10. The method of inserting the treatment tool according to claim 1, wherein the guide wire extending out from the duodenal papilla is pulled into the second channel by gripping the guide wire with a gripping forceps inserted into the second channel.

11. The method of inserting the treatment tool according to claim 2, wherein the cylindrical-shaped treatment tool is inserted up to the position of the biliary tract including the stenosis portion via the guide wire pulled into the second channel.

12. The method of inserting the treatment tool according to claim 2, wherein the cylindrical-shaped treatment tool is a stent.

* * * * *